US012728167B2

(12) United States Patent
Odorisio et al.

(10) Patent No.: US 12,728,167 B2
(45) Date of Patent: Sep. 8, 2026

(54) COMPOSITIONS OF TRI-SUBSTITUTED STARCH AND METHODS FOR MAKING AND USING THE SAME

(71) Applicant: CORN PRODUCTS DEVELOPMENT, INC., Westchester, IL (US)

(72) Inventors: Christina Odorisio, Bridgewater, NJ (US); Maria Stewart, Bridgewater, NJ (US)

(73) Assignee: Corn Products Development, Inc., Westchester, IL (US)

( * ) Notice: Subject to any disclaimer, the term of this patent is extended or adjusted under 35 U.S.C. 154(b) by 702 days.

(21) Appl. No.: 17/925,942

(22) PCT Filed: May 24, 2021

(86) PCT No.: PCT/US2021/033819
§ 371 (c)(1),
(2) Date: Nov. 17, 2022

(87) PCT Pub. No.: WO2021/247263
PCT Pub. Date: Dec. 9, 2021

(65) Prior Publication Data

US 2023/0190942 A1 Jun. 22, 2023

Related U.S. Application Data

(60) Provisional application No. 63/034,144, filed on Jun. 3, 2020.

(51) Int. Cl.
*A61K 47/61* (2017.01)
*A61P 1/14* (2006.01)

(52) U.S. Cl.
CPC ................ *A61K 47/61* (2017.08); *A61P 1/14* (2018.01)

(58) Field of Classification Search
CPC ...................................................... A61K 47/61
USPC ........................................................... 514/60
See application file for complete search history.

(56) References Cited

U.S. PATENT DOCUMENTS

| | | | | |
|---|---|---|---|---|
| 4,059,458 A * | 11/1977 | Germino | ................ | C09K 23/34<br>106/206.1 |
| 5,587,412 A | 12/1996 | Borchers et al. | | |
| 5,656,682 A | 8/1997 | Rimsa et al. | | |

FOREIGN PATENT DOCUMENTS

| | | | |
|---|---|---|---|
| EP | 1142911 A1 | | 10/2001 |
| JP | 2000-159801 | | 6/2000 |
| JP | 2006-299271 | | 11/2006 |
| WO | 95/13801 | | 5/1995 |
| WO | 01/02016 | | 1/2001 |
| WO | WO 2018/027274 | * | 2/2018 |

OTHER PUBLICATIONS

Difilippo, S. et al., "Organocatalytic route for the synthesis of propionylated starch", Carbohydrate Polymers, Applied Science Publishers, Ltd Barking, GB, vol. 137, Oct. 22, 2015, pp. 198-206.
Annison, et al. "Acetylated, Propionylated or Butyrylated Starches Raise Large Bowel Short-Chain Fatty Acids Preferentially When Fed to Rats", Journal of Nutrition, 2003, v. 133, pp. 3523-2538.

* cited by examiner

*Primary Examiner* — Yih-Horng Shiao

(57) ABSTRACT

Disclosed herein are compositions containing a modified starch, the starch modified to contain ester linkages to multiple short-chain fatty acids of different lengths; in particular, containing linkages to acetate, propionate, and butyrate. Methods for making and using such starch esters are described, as are compositions including the starch ester for nutritional effects and health benefits.

17 Claims, 15 Drawing Sheets

COMPOSITIONS OF TRI-SUBSTITUTED STARCH AND METHODS FOR MAKING AND USING THE SAME

This application is a U.S. National Stage application under 35 U.S.C. § 371 of International Application No. PCT/US2021/033819, filed May 24, 2021, which claims priority to United States Provisional Patent Application Ser. No. 63/034,144 filed Jun. 3, 2020, all of which are incorporated herein by reference in their entirety.

Described herein are starch-containing compositions comprising a starch material modified to form ester bonds with multiple short chain fatty acids (SCFA) of different lengths. The present invention relates to tri-modified starch compositions useful in nutritional applications. The invention further relates to methods of making and using the compositions.

Short-chain fatty acids (SCFAs), particularly acetate, propionate and butyrate, are the primary end products resulting from intestinal microbial fermentation of dietary fibers and digestion-resistant starch (Bajka et al., *Nutrition Research,* 2010, 30(6); 427-34). Deficiencies of SCFAs within blood plasma and the colon have been associated with metabolic and autoimmune disorders. For example, inhibition of SCFA synthesis by antibiotics can result in diarrhea (Binder H. J., *Annu Rev Physiol.,* 2010;72:297-313). Maintaining optimal levels of colonic SCFAs may prevent and counteract such disorders and associated diseases, such as obesity, type 2 diabetes, inflammation, inflammatory bowel disease, irritable bowel syndrome, diarrhea, atherosclerosis, Crohn's disease and ulcerative colitis.

Digestion-resistant carbohydrates (dietary fibers) modified to be either acetylated or butyrylated have been shown to effect protection from autoimmune disease in NOD mice (see WO2018/027274, published 02/15/2018). Moreover, acetylated starch molecules have been shown to increase pools of acetate within the bowel of rats (A. R. Bird et al., Food Hydrocolloids, 20 (2006):1135-40). However, these synthesis reactions typically require the use of dimethylsulfoxide, or DMSO, to attach acetyl or butyryl moieties. There exists a need to provide such modified molecules that are made in the absence of DMSO or other solvents for, for example, dietary or nutritional applications, as it is generally desirable to limit the amount of DMSO or other solvent present in preparations for human consumption. For some applications, it is preferred for such preparations to be free of certain solvents entirely, especially DMSO.

In addition to modifications made to starch that covalently attaches a single species or type of SCFA, there has also been work in esterification of more than a single species or type of SCFA onto a starch molecule. See, for example, U.S. Pat. No. 5,587,412, issued Dec. 24, 1996, where corn starch was esterified with acetate and either propionate or butyrate. However, those molecules required a large degree of substitution, of at least about 1.8, to provide particles having good dimensional stability and physical properties.

There exists a need for improved health compositions that provide superior levels of SCFAs to the colon of a user.

The present disclosure relates to modified starch compositions useful in nutritional formulations. In particular, the present disclosure relates to compositions comprising a starch ester, that is a starch substituted or modified to be bound to multiple short chain fatty acids of different lengths. The starch ester can contain at least three different species of SCFA. In some embodiments, such starch ester arises from a starch that is tri-substituted with acetate, propionate and butyrate. The disclosure also relates to methods of making and using the compositions.

Disclosed herein are starches that have been subjected to modification to incorporate multiple SCFAs of different lengths. In some aspects, the starch ester includes at least three different SCFAs. Such starch ester may provide a vehicle for delivering one or more SCFAs.

In certain exemplary aspects, the invention includes a composition comprising a starch ester, wherein the starch ester is the product of modification of a starch with acetic acid, propionic acid, and butyric acid. In certain aspects, such tri-substituted starch ester compositions can result in the production of different SCFAs by colon microbes.

In certain aspects, the invention includes methods making multi-substituted starch esters, by mixing starch with short chain fatty acids; adding an esterification catalyst; and mixing the composition. In certain aspects, the method is performed in an absence of DMSO.

In certain aspects, the invention includes a nutritional or pharmaceutical formulation including the starch ester. In certain aspects, the invention includes the use of starch ester to treat a number of disorders associated with the digestive tract.

In certain aspects, the invention includes methods of using the composition described herein to achieve an increased short chain fatty acid concentration within a user's colon. In certain aspects, the invention includes a method for treating an autoimmune or metabolic disorder in a subject by the administration to the subject of a therapeutically effective amount of a composition or formulation as described herein.

BRIEF DESCRIPTION OF THE DRAWINGS

While the attached drawings show, describe and point out novel features as applied to various embodiments, it will be understood that various omissions, substitutions, and changes in the form and details of the compositions and methods may be made without departing from the spirit of the disclosure. The figures herein are illustrative in nature and are not intended to be limiting. As will be recognized, certain embodiments described herein may be embodied within a form that does not provide all of the features and benefits set forth herein, as some features may be used or practiced separately from others.

Figure 1:
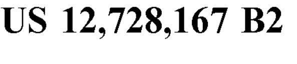
FIG. 1 shows a gel permeation chromatograph of native corn starch used as a base material.

The present technology is not to be limited in terms of the aspects described herein, which are intended as illustrations of aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to methods, conjugates, reagents, compounds, or compositions, which can, of course, vary. All methods described herein can be performed in any suitable order unless otherwise indicated herein or otherwise clearly contradicted by context. It is also to be understood that the terminology used herein is for the purpose of describing aspects only and is not intended to be limiting. Thus, it is intended that the specification be considered as exemplary only with the breadth, scope and spirit of the present technology indicated only by the appended claims, definitions therein and any equivalents thereof.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure. In the event of a conflict in a definition in the present disclosure and that of a cited reference, the present disclosure controls.

The embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

As will be understood by one skilled in the art, for any and all purposes, particularly in terms of providing a written description, all ranges disclosed herein also encompass any and all possible subranges and combinations of subranges thereof. As used throughout, ranges are used as shorthand for describing each and every value that is within the range. Any value within the range may be selected as the terminus of the range. All language such as "up to," "at least," "greater than," "less than," and the like, include the number recited and refer to ranges which can be subsequently broken down into subranges as discussed above.

Use of "about" or "similar" to modify a number in this specification is meant to include the number recited plus or minus 10%. Where legally permissible recitation of a value in a claim means about the value. Use of about in a claim or in the specification is not intended to limit the full scope of covered equivalents.

The term "short-chain fatty acid" or "SCFA" may be used interchangeably and may refer to fatty acids containing fewer than six carbon atoms or having a molecular backbone containing fewer than 6 carbons. Different SCFAs can be described as having different numbers of carbons or different lengths. For example, acetate has a molecular backbone containing two carbons, propionate has a molecular backbone containing three carbons, and butyrate has a molecular backbone containing four carbons. Each of these three SCFAs contains a different number of carbons in its chemical or molecular structure and thus, these three SCFAs may be considered to have different lengths than each other.

The term "starch ester" may refer to any starch, including a native starch or a modified starch derivative of any origin, or combination thereof, that comprises an ester group. In some embodiments, such starch ester includes starches modified to contain one or more types of SCFA. The ester groups of the starch esters of the present invention will comprise—or consist of—fatty acids having a carbon chain of 6 or fewer carbon atoms. For example, the ester groups may comprise formic acid, acetic acid, propionic acid, butyric acid, isobutyric acid, valeric acid, isovaleric acid, and mixtures thereof.

The term "tri-substituted starch ester" or "tri-modified starch ester" may be used interchangeably and may refer to a starch ester containing at least three SCFAs of different lengths. For example, a tri-substituted starch ester can contain starch molecules having ester linkages to acetate, propionate, and butyrate molecules. Individual starch molecules within the starch material may contain ester linkages to zero, one, two, or three SCFA sub stituents, while the aggregate starch material contains ester linkages to acetate, propionate and butyrate molecules. Individual glucose units within any starch molecule may each contain ester linkages to zero, one, two, or three SCFA substituents. Where an individual glucose unit contains multiple SCFA substituents, those substituents may be the same or different SCFA.

The term "mono-substituted starch ester" may refer to a starch ester modified to contain a single species or type of SCFA, while a "di-substituted starch ester" may refer to a starch ester modified to two SCFAs of different length, and so on.

The "degree of substitution" (DS) of a polymer may refer to the average number of substituent groups attached per base or monomeric unit. A starch molecular may contain a chain of connected glucose sugars. In an esterified starch or a starch ester, the DS may indicate the average number of hydroxyl groups substituted with an SCFA for each glucose backbone molecule of the starch.

The term "crystalline granular structure" or "crystalline structure" may be used interchangeably and may refer to the appearance of starch or starch granules having a highly ordered structure. Such structure may be discerned via microscopic examination, by for example, light microscopy and scanning electron microscopy, such as described for example in Starches: Practical Guides for the Food Industry by David J. Thomas and William A. Atwell (Eagan Press 1999) at pp. 13-15.

The term "gelatinization temperature" of a starch molecule may refer to the temperature at which the molecular order within the starch molecule is disrupted, resulting in irreversible changes in properties including loss of crystalline structure, loss of birefringence, and viscosity.

The terms "treatment," "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a subject and includes: (a) preventing a disease from occurring in a subject whom may be predisposed to the disease; (b) inhibiting the disease, i.e. arresting its development; (c) relieving the disease, i.e. causing regression of the disease; or (d) reducing the symptoms associated with the disease.

The terms "effective amount" and "pharmaceutically effective amount" refer to a sufficient amount of an agent to provide the desired biological result. That result can be reduction and/or alleviation of a sign, symptom, or cause of a disease or disorder, or any other desired alteration of a biological system. An appropriate effective amount in any individual case may be determined by one of ordinary skill in the art using routine experimentation. A "therapeutically effective amount" refers to that amount which provides a therapeutic effect for a given condition and administration regimen. In particular, "therapeutically effective amount" means an amount that is effective to prevent, alleviate or ameliorate symptoms of the disease or prolong the survival of the subject being treated, which may be a human or non-human animal. Determination of a therapeutically effective amount is within the skill of the person skilled in the art.

The terms "nutritional formulation" mean any composition that either satisfies the nutrient requirements of a subject or supplements the diet of a subject. Such nutritional formulations may promote general health in a number of ways such as to reduce autoimmune and inflammatory responses, enhance immune strength, promote weight loss or appetite suppression, improve overall gut health, enhance weight maintenance or weight gain, and manage chronic diseases such as diabetes, hypertension, and digestive disorders. By promoting, the uptake of vitamins, minerals, proteins, amino acids, or other substances as needed, nutritional formulations may promote general health in a number of ways in many populations.

The term "digestion-resistant" may refer to foods or food components, or portions thereof, that pass through a digestive tract without being digested or absorbed by the digestive tract. Certain polysaccharides and carbohydrates, which includes certain native and modified starches and fibers, are partially or completely unaffected by digestive enzymes and chemicals found in the stomach, small intestine, and large intestine. Digestion-resistant foods and carbohydrates of particular interest include starch esters that are resistant to digestion in different parts of the gastrointestinal tract, such as the small and large intestines. Some embodiments of the present inventive technology relate to compositions including digestion-resistant starches which are modified to contain ester linkages with short chain fatty acids (SCFAs). Digestion-resistant carbohydrates of particular interest include starches that are resistant to digestion in different parts of the gastrointestinal tract, such as the small or large intestines. Such modified starches are useful in nutritional formulations, which can deliver SCFAs to the colon of a subject.

Without being bound to theory, it is believed that SCFAs released from bacterial fermentation of dietary fiber in the colon may promote gut health in a subject in numerous ways. For example, these fatty acids are thought to be important for maintaining visceral function by increasing blood flow, contribute to improved electrolyte and fluid absorption during diarrhea, maintenance of low colonic pH to limit the growth of intestinal pathogens and also the modulation of colonic muscular activity. These properties may be achieved when compositions containing starches comprising one or more types of SCFA are delivered to the cells of the digestive system, such as the cells resident in the colon.

In certain embodiments, the digestion-resistant carbohydrate may include polysaccharides and oligosaccharides including, for example, cellulose, hemicellulose, pectins, arabinoxylans, xyloglucans, glucomannans, galactomannans, galactan, (3-glucans, pectic polysaccharides (homogalacturonan, rhamnogalacturonan-I, and rhamnogalacturonan-II), resistant maltodextrin, fructooligosaccharides, inulin, galactooligosaccharides, mannanoligosaccharides, arabinooligosaccharides, and xylooligosaccharides. Such digestion-resistant carbohydrates may provide sources of dietary fiber that are fermented by colon microbial cells to produce short chain fatty acids.

In certain embodiments, the digestion-resistant carbohydrate may contain starch and may comprise digestion-resistant starch. The starch material used herein may be any of several starches or mixtures thereof. The starches can be native starches or starches that have been modified by any process, including but not limited to chemical, enzymatic, and physical treatment, as described for example in Starches: Practical Guides for the Food Industry by David J. Thomas and William A. Atwell (Eagan Press 1999).

Some embodiments relate to a tri-substituted starch ester or a composition containing a tri-substituted starch ester; that is, a starch molecule modified to be bound to at least three SCFAs of different lengths. In some embodiments, the starch ester may comprise three or more SCFAs chosen from formate, acetate, propionate, butyrate, isobutyrate, valerate, and isovalerate. In some embodiments, SCFAs having high bioavailability may be chosen. In some embodiments, a modified starch ester may provide starch molecules having ester linkages to acetate, propionate, and butyrate molecules. In some embodiments, the three or more SCFAs consist of acetate, propionate, and butyrate.

SCFAs are important to gastrointestinal health. They can be provided naturally by the microbial fermentation of digestion-resistant foods in the small or large intestines. SCFAs may occur as end products of such bacterial carbohydrate fermentation of digestion-resistant foods. It would be desirable to provide a tri-substituted starch ester to deliver SCFAs at increased levels, levels sufficient to provide a therapeutic effect as described herein.

In some embodiments, the starch ester may comprise glucose molecules with one or more hydroxyl groups substituted with a variety of SCFAs. Where an unmodified starch molecule may have a degree of substitution of zero. In a modified starch molecule, each glucose subunit may have one or more hydroxyl groups substituted with a substituent. In such a modified starch ester, the starch ester may have a degree of substitution of about 0.01 to about 0.6, or about 0.01 to about 0.4, or about 0.1 to about 0.6, or about 0.1 to about 0.5, or about 0.1 to about 0.4, or about 0.1 to about 0.3, or about 0.2 to about 0.3.

Certain embodiments provide a composition comprising digestion-resistant carbohydrate, wherein the digestion-resistant carbohydrate comprises starch ester. In certain embodiments, the invention includes a composition comprising a starch ester, wherein the starch ester is the product of esterification of a starch molecule with acetic acid, propionic acid, and butyric acid. In certain embodiments, the invention includes a composition comprising a starch ester, wherein the starch ester is modified to contain acetate, propionate, and butyrate groups.

In certain embodiments, the invention includes a composition comprising a starch ester, wherein the starch ester is the product of esterification of starch with acetic acid, propionic acid, and butyric acid, and wherein the composition contains less than 0.01% dimethyl sulfoxide (DMSO). In some embodiments, the starch ester or the composition may contain less than 1%, less than 0.1%, or less than 0.01% of dimethyl sulfoxide, or no dimethyl sulfoxide.

The starch may have a granular, crystalline structure or non-granular, amorphous structure, or both.

As used herein, modified starches are intended to include, without limitation, cross-linked starches, thermally inhibited starches, stabilized starches, acetylated and organically esterified starches, hydroxylethylated and hydroxylpropylated starches, phosphorylated and inorganically esterified starches, cationic, anionic, nonionic, and zwitterionic starches, and succinate and substituted succinate derivatives of starch. For example, the starch may be oxidized, thinned, and/or cross-linked. The starch may also be reacted with cationic, anionic, amphoteric, and/or non-ionic agents.

Starches include, but are not limited to, those derived from any plant source including starches selected from corn or maize starch, pea starch, bean starch, potato starch, wheat starch, oat starch, rice starch, rye starch, sago starch, tapioca starch, wheat starch, waxy corn starch, high amylose corn starch, waxy potato starch, waxy rice starch, and sorghum starch, and mixtures thereof. Starches may be selected from corn, pea, potato, wheat, oats, rice, rye, sago, tapioca, wheat, waxy starches such as waxy corn, waxy potato and waxy rice, sorghum and high amylose corn (having high amylose starch, i.e., starch having at least 40%, and more particularly, at least 65% amylose content by weight), and any derivatives or combinations thereof. The amylose content of such high amylose corn starch may be at least about 70% by weight with respect to that of the starch. Starch flour may also be used. In certain embodiments, the starch may be a native starch like HYLON® VII, corn starch. (Ingredion, Westchester, Ill.).

In certain embodiments, the digestion-resistant carbohydrate may include carbohydrates that resist or escape digestion and absorption in the small intestine. In some embodiments, the digestion-resistant carbohydrate may include one or more of digestion-resistant oligosaccharides (for example, carbohydrates with a degree of polymerization between three and ten), resistant starch and non-starch polysaccharides. In certain embodiments the carbohydrate may be VERSAFIBE™, dietary fiber (Ingredion, Westchester, Ill.). In certain embodiments, digestion-resistant carbohydrate may include non-starch polysaccharides such as cellulose, hemicellulose (composed of a variety of heteropolysaccharides including arabinoxylans), β-glucan and pectins.

When a composition containing a starch is introduced to an in vitro model colon cell assay, it may induce the model colon cells to make or provide one or more SCFAs over a period of time. Compositions containing the tri-substituted starch ester may induce the model colon cells to produce different amounts of the one or more SCFAs, compared to compositions containing a non-esterified starch or a mono-substituted starch ester containing only one short chain fatty acid. In some embodiments the mono-substituted starch ester contains one of the SCFAs contained in the starch ester. In some embodiments, the mono-substituted starch ester contains one of the SCFAs contained in the starch ester. In some embodiments, the mono-substituted starch ester has a degree of substitution similar to the tri-substituted starch ester.

In some embodiments, the model colon cells are exposed to or incubated with the starch ester for about 0.5 hour, 1 hours, 3 hours, 6 hours, 12 hours, 18 hours, 20 hours, 24 hours, or 48 hours, to induce the production of SCFAs by the model colon cells.

In some embodiments, the starch ester may be used to achieve an increased amount of one or more SCFAs within a user's colon. Still other embodiments describe a formulation comprising a starch ester as described herein.

In general, starch esters can be made by reacting a starch and one or more SCFAs in the presence of a catalyst in a solvent for the starch ester. In some embodiments, the esterification catalyst may comprise two or more catalysts. Some embodiments relate to a method of producing or making a starch ester, the method comprising; a) mixing a starch with one or more short chain fatty acids; b) adding an esterification catalyst, to provide mixture; c) mixing the mixture; and d) optionally, heating the mixture; wherein the method is performed in the absence of DMSO.

In some embodiments, the method can incorporate the one or more short chain fatty acids is selected from formate, acetate, propionate, butyrate, isobutyrate, valerate, and isovalerate. In some embodiments, the method can incorporate one, two, there, four, five, six, or more different SCFAs. In some embodiments, the method can incorporate at least acetate, propionate, and butyrate.

Dimethyl sulfoxide (DMSO) is widely available as a solvent but its medical use is restricted by the FDA. Adverse reactions to DMSO are common but are usually minor and related to the concentration of DMSO in the medication solution. Further, for compositions ingested by individuals, the use of a solvent such as DMSO is disfavored by some consumers. Methods to detect DMSO in solution are generally known to one of skill in the art. In some preferred embodiments, compositions of the present invention contain less than 0.01% DMSO. In some embodiments, the composition contains or is made with less than 1%, less than 0.1%, or less than 0.01% of dimethyl sulfoxide, or no dimethyl sulfoxide.

In some embodiments, the method can provide a starch ester having a granular, crystalline structure or non-granular, amorphous structure, or both.

In some embodiments, the method may provide the starch ester having a degree of substitution of about 0.01 to about 0.6, or about 0.01 to about 0.4, or about 0.1 to about 0.6, or about 0.1 to about 0.5, or about 0.1 to about 0.4, or about 0.1 to about 0.3, or about 0.2 to about 0.3.

Esterifying agents may refer to any organic anhydrides. Organic anhydrides may include, but not be limited to, acetic anhydride, propionic anhydride, butyric anhydride, hexanoic anhydride, maleic anhydride, phthalic anhydride, succinic anhydride, hexenyl succinic anhydride, octenyl succinic anhydride, dodecenylsuccinic anhydride, hexadecenyl succinic anhydride, and mixtures thereof.

The esterification process may include the use of a catalyst. A catalyst may include any material that can catalyze the esterification reaction. The catalyst may be organic or inorganic, acidic or basic. Acidic catalysts may include, but not be limited to, sulfuric acid, perchloric acid, hydrochloric acid, methane sulfonic acid, dodecyl benzene sulfonic acid, benzene sulfonic acid, toluene sulfonic acid, strong-acid ion exchange resin, phosphoric acid, and mixtures thereof. Basic catalysts may include, but not be limited to, sodium hydroxide, sodium acetate, sodium carbonate, sodium bicarbonate, pyridine, and mixtures thereof. In one embodiment, sulfuric acid is used. The amount of catalyst should be sufficient to catalyze the esterification reaction.

In some embodiments, the method may use an esterification catalyst such as sulfuric acid, perchloric acid, hydrochloric acid, methane sulfonic acid, dodecyl benzene sulfonic acid, benzene sulfonic acid, toluene sulfonic acid, strong-acid ion exchange resin, phosphoric acid, and mixtures thereof. In some embodiments, the method may use that esterification catalyst at between about 0.1 and about 1.0 mol %, between about 0.1 and about 0.8 mol %, between about 0.1 and about 0.6 mol %, between about 0.1 and about 0.5 mol %, between about 0.2 and 1. about 0 mol %, between about 0.2 and about 0.8 mol %, or between about 0.25 and about 0.5 mol %.

In some embodiments, the method may require one or more SCFAs selected from formate, acetate, propionate, butyrate, isobutyrate, valerate, and isovalerate. In some embodiments, three or more SCFAs are selected from formate, acetate, propionate, butyrate, isobutyrate, valerate, and isovalerate. In some embodiments, the three or more SCFAs comprise acetate, propionate, and butyrate. In some embodiments, the three or more SCFAs consist of acetate, propionate, and butyrate.

Still other embodiments describe a starch ester obtainable by, or obtained by, from one or more method described herein. In some embodiments, the formulations may comprise, for example, a nutritional formulation, a pharmaceutical formulation, and formulation for therapeutic or medical applications.

The starch ester provided by the methods described herein can provide delivery of SCFAs to the colon of a subject. The SCFAs may be provided to an individual requiring treatment by any number of means known to the skilled person. For example, in some embodiments, the SCFAs are provided in a pharmaceutical formulation for oral, local or systemic administration, as described herein. In some embodiments, and as described herein, the pharmaceutical formulation is adapted for delivery of the SCFAs to the large intestine, more particularly, the colon of the individual. In some embodiments, a formulation can include a composition containing the starch esters described herein.

Alternatively, the starch ester be added to the individual's diet to provide SCFAs to the individual, whereby the SCFAs are provided for contact with the cells of the digestive tract upon digestion of a dietary agent in a desired region of the gastrointestinal tract. In some embodiments, the dietary agent provides for release of the SCFAs in the colon, as described herein. Alternatively, the SCFAs may be provided to the individual as a supplement to an individual's diet, whereby the SCFAs are provided for contact with the cells of the digestive tract upon digestion of a dietary supplement in a desired region of the gastrointestinal tract. In some embodiments, the dietary supplement provides for release of the SCFAs in the colon, as described herein.

In certain embodiments, the composition induces greater amounts of acetate after 6 hours of incubation in an in vitro model colon assay, when compared to the amounts of acetate induced by the same concentration of a starch ester having a similar DS but esterified to contain only a single SFCA, such as acetate. In certain embodiments, the composition induces greater amounts of propionate after 6 hours of incubation in an in vitro model colon assay, when compared to the same concentration of a starch ester having a similar DS but esterified only with a single SFCA, such as propionate. In certain embodiments, the composition induces greater amounts of propionate after 6 hours of incubation in an in vitro model colon assay, when compared to the same concentration of a starch ester having a similar DS but esterified only with a single SFCA, such as butyrate. In certain embodiments, the composition induces greater amounts of propionate after 20 hours of incubation in an in vitro model colon assay, when compared to the same concentration of a starch ester having a similar DS but esterified only with a single SFCA, such as acetate, butyrate, or propionate.

In certain embodiments, an object is the use of a composition comprising the starch ester to achieve an increased concentration of one or more short chain fatty acids within a user's colon. Such increase of the SCFAs to the colon of a subject may act as a treatment. In certain embodiments, use may encompass formulating a pharmaceutical or nutritional formulation comprising the disclosed tri-substituted starch and ingesting such formulation. In some embodiments, use encompasses a subject ingesting concentrates, such as in a pill or powder form, of the disclosed tri-substituted starch.

In some embodiments, the starch ester may possess particular enthalpic qualities. It may require different amounts of energy to gelatinize one gram of a composition containing a starch ester, compared to the amount of energy required to gelatinize one gram of the unesterified version of the starch ester. It may require a different amount of energy to gelatinize one gram of a composition containing a tri-substituted starch ester compared to a mono-substituted starch ester. For example, to gelatinize one gram of a composition containing the starch ester, it may require between about 0.1 to about 10.0 J/g, or between about 0.5 to about 10.0 J/g, or between about 0.5 to about 5.0 J/g, or between about 0.5 to about 4.0 J/g, or between about 1.0 to about 10.0 J/g, or between about 1.0 to about 5.0 J/g, or between about 1.0 to about 4.0 J/g, or between about 2.0 to about 4.0 J/g, or between about 3.0 to about 5.0 J/g. to gelatinize one gram of the composition, compared to a control starch molecule that is not esterified.

In certain embodiments, a formulation may contain a starch ester described herein.

Certain embodiments may provide a method for providing a nutritional supplement in support of gut health in a subject, the method comprising administering to the subject an effective amount of the composition. In certain embodiments, the composition comprising the starch ester is a nutritional formulation. The nutritional formulation may be nutritionally complete and contain suitable types and amounts of free amino acids, lipids, carbohydrates, vitamins and minerals. In certain embodiments, the nutritional formulation may be in the form of liquids, powders, gels, pastes, solids, tablets, capsules, concentrates, suspensions, or ready-to-use forms of enteral formulas, oral formulas, formulas for infants, formulas for pediatric subjects, formulas for children, and/or formulas for adults. In certain embodiments, the nutritional formulation can be a liquid (ready-to-use or concentrated) or powder. In certain embodiments, beneficial formulations consisting of the novel starch ester include supplements, nutritional drinks, nutritional bars, and readily dispersed powders. If the nutritional formulation is a liquid, the shelf life of the nutritional formulation is at least 18 months. If the nutritional formulation is a powder, the shelf life of the nutritional formulation is at least 24 months.

In certain embodiments, the starch ester may be added to one or more of a standard infant formula, a hydrolyzed protein infant formula, a lactose-free infant formula, a soy protein infant formula, a hydrolyzed soy protein infant formula, or any nutritional formulation which requires the benefit of delivering SCFAs to the colon.

In certain embodiments, the starch ester constitutes 0.5-50% of the nutritional formulation. In certain embodiments, the starch ester constitutes 0.5-30% of the nutritional formulation. In certain embodiments, the starch ester constitutes 0.5-20% of the nutritional formulation. In certain embodiments, the starch ester constitutes 0.5-10% of the nutritional formulation. In certain embodiments, the starch ester constitutes 0.5-5% of the nutritional formulation.

The methods of the present invention are useful for the prevention and/or treatment of any disease which results in an increased autoimmune inflammatory response in one or more regions of the body. The methods of the present invention are therefore useful for treating diseases associated with dysfunctional/ineffective regulatory T cell function, expanded autoreactive T effector cells, and/or B cell dysfunction. Diseases which may be prevented and/or treating in accordance with the present invention include but are not limited to autoimmune diseases, including, for example, an autoimmune disease selected from the group consisting of type 1 diabetes, psoriasis, rheumatoid arthritis, inflammatory bowel disease, caeliac disease, autoimmune hepatitis, myocarditis, lupus nephritis, primary biliary cirrhosis and multiple sclerosis.

In certain embodiments, an object includes a method for treating an autoimmune or metabolic disorder in a subject, the method comprising administering to the subject a therapeutically effective amount of a composition comprising starch ester. In certain embodiments, the disorder is selected from obesity, diabetes, inflammation, inflammatory bowel disease, irritable bowel syndrome, diarrhea, atherosclerosis, Crohn's disease and ulcerative colitis.

The inventive technology is further described in the following aspects, which are intended to be illustrative, and are not intended to limit the full scope of the claims and their equivalents.

Subject matter contemplated by the present disclosure is set out in the following numbered embodiments:

1. A starch ester, the starch ester comprising a starch and at least three short chain fatty acids chosen from formate, acetate, propionate, butyrate, isobutyrate, valerate, and isovalerate;

preferably, wherein the at least three short chain fatty acids comprise acetate, propionate, and butyrate.

2. The starch ester of embodiment 1, wherein the starch ester has a degree of substitution of about 0.01 to about 0.6, or about 0.01 to about 0.4, or about 0.1 to about 0.6, or about 0.1 to about 0.5, or about 0.1 to about 0.4, or about 0.1 to about 0.3, or about 0.2 to about 0.3;

preferably, wherein the degree of substitution is about 0.1 to about 0.6.

3. The starch ester of any preceding embodiment, wherein the starch ester contains less than 1%, less than 0.1%, or less than 0.01% of dimethyl sulfoxide, or no dimethyl sulfoxide;

preferably, wherein the starch ester contains less than 0.01% of dimethyl sulfoxide.

4. The starch ester of any preceding embodiment, wherein the starch ester comprises a crystalline granular structure;

preferably, wherein the starch ester comprises acetic acid, propionic acid, and butyric acid; and preferably, wherein the starch is selected from corn starch, pea starch, bean starch, potato starch, wheat starch, oat starch, rice starch, rye starch, sago starch, tapioca starch, wheat starch, waxy corn starch, high amylose corn starch, waxy potato starch, waxy rice starch, and sorghum starch, and mixtures thereof; wherein, optionally, the starch comprises high amylose corn starch.

5. The starch ester of any preceding embodiment, wherein the starch ester provides a first amount of a short chain fatty acid in an in vitro model colon assay that is greater than a second amount of the short chain fatty acid provided by a control composition, the control composition comprising a monosubstituted or di-substituted starch ester.

6. The starch ester of embodiment 5, wherein the starch ester is incubated in the in vitro model colon assay for about 0.5 hour, 1 hours, 3 hours, 6 hours, 12 hours, 18 hours, 20 hours, 24 hours, or 48 hours;

preferably, wherein the starch ester is incubated in the in vitro model colon assay for about 6 hours or 24 hours;

preferably, wherein the starch ester of embodiment 5, wherein the mono-substituted or di-substituted starch ester having a similar degree of substitution as the starch ester.

7. The starch ester of any preceding embodiment, wherein the starch ester requires between about 0.1 to about 10.0 J/g, or between about 0.5 to about 10.0 J/g, or between about 0.5 to about 5.0 J/g, or between about 0.5 to about 4.0 J/g, or between about 1.0 to about 10.0 J/g, or between about 1.0 to about 5.0 J/g, or between about 1.0 to about 4.0 J/g, or between about 2.0 to about 4.0 J/g, or between about 3.0 to about 5.0 J/g to gelatinize one gram of the starch ester, compared to a control starch molecule that is not esterified;

preferably, wherein the starch ester requires between about 0.5 to about 5.0 J/g.

8. Use of the starch ester of any one of embodiments 1 to 7 to achieve an increased amount of the short chain fatty acid within a user's colon.

9. A method for producing a starch ester, the method comprising;
   a) mixing a starch with one or more short chain fatty acids;
   b) adding an esterification catalyst, to provide a mixture;
   c) mixing the mixture; and
   d) optionally, heating the mixture;
   wherein the method is performed in the absence of DMSO.

10. The method of embodiment 9, wherein the one or more fatty acids is selected from formate, acetate, propionate, butyrate, isobutyrate, valerate, and isovalerate;

preferably, wherein the one or more short chain fatty acids comprise acetate, propionate, and butyrate.

11. The method of any one of embodiments 9 to 10, wherein the method is performed under anhydrous conditions.

12. The method of any one of embodiments 9 to 11, wherein the starch ester has a degree of substitution of about 0.05 to about 0.5, about 0.1 to about 0.4, about 0.1 to about 0.3, or about 0.2 to about 0.3;

preferably, wherein the degree of substitution is about 0.1 to about 0.6; and preferably, wherein the starch ester is in a crystalline granular structure.

13. The method of any one of embodiments 9 to 12, wherein the esterification catalyst is selected from sulfuric acid, perchloric acid, hydrochloric acid, methane sulfonic acid, dodecyl benzene sulfonic acid, benzene sulfonic acid, toluene sulfonic acid, strong-acid ion exchange resin, phosphoric acid, and mixtures thereof; preferably, wherein the esterification catalyst is sulfuric acid; and wherein the esterification catalyst is used at between about 0.1 and about 1.0 mol %, between about 0.1 and about 0.8 mol %, between about 0.1 and about 0.6 mol %, between about 0.1 and about 0.5 mol %, between about 0.2 and 1. about 0 mol %, between about 0.2 and about 0.8 mol %, or between about 0.25 and about 0.5 mol %; preferably, wherein the esterification catalyst is used at between about about 0.1 and about 0.5 mol %.

14. The method of any of embodiments 9 to 13, wherein the starch ester comprises at least three short chain fatty acids chosen from formate, acetate, propionate, butyrate, isobutyrate, valerate, and isovalerate;

preferably, wherein the at least three short chain fatty acids comprise acetate, propionate, and butyrate.

15. The starch ester obtainable by the method of any one of embodiments 9 to 14.

16. A composition comprising the starch ester of any one of embodiments 1 to 7 and embodiment 15; preferably wherein the composition comprises a nutritional formulation or a pharmaceutical formulation.

17. A method for providing a nutritional supplement in support of gut health in a subject, the method comprising administering to the subject an effective amount of the starch ester as described in any one of embodiments 1 to 7 and embodiment 15.

18. A method for treating an autoimmune or metabolic disorder in a subject, the method comprising administering to the subject an effective amount of the starch ester as described in any one of embodiments 1 to 7 and embodiment 15;

preferably, wherein the disorder is selected from obesity, diabetes, inflammation, inflammatory bowel disease, irritable bowel syndrome, diarrhea, atherosclerosis, Crohn's disease and ulcerative colitis.

EXAMPLES

The technology is further described by the following examples, which are intended to be illustrative and are not intended to limit the full scope of the claims or their equivalents.

Example 1: Preparation of Starch Acetate under Anhydrous Conditions

In a round bottom flask equipped with magnetic stir bar, 61mL of glacial acetic acid was added. The bottom of the flask was submersed into a water-filled dish set on top of a stir plate. Next, 50 g of anhydrous corn starch (HYLON® VII, corn starch, Ingredion Inc.) was added under light agitation and mixed for 10-15 minutes.

A catalyst was prepared by slowly mixing 10m1 of glacial acetic acid with an amount of sulfuric acid (between 0.1-0.5 mol %). That mixture was then slowly added to the round bottom flask containing glacial acetic acid and starch to achieve a final sulfuric acid concentration of 0.1-0.5 mol %. Once the temperature stabilized, the flask was transferred to an oil bath and heated to 85° C. The mixture was allowed to react for 2-8 hr at 80° C. The product was then slowly transferred to 500 mL of water and mixed on a stir plate. An additional 400mL of water was used to collect and quantitatively transfer residual product.

To de-water the product, the mixture was poured through a Buchner funnel containing a filter. The product starch cake was washed three times using 400mL of water, or until a pH of 5-6 was achieved. The cake was crumbled and allowed to dry in a hood overnight.

Example 2: Preparation of Mono-Substituted Starch under Anhydrous Conditions A desired amount of anhydrous starch was measured to achieve a 0.81:1 molar ratio of acetic acid:starch and transferred to a 400 mL Griffin beaker equipped with overhead stir motor and Teflon paddle. Next, using a graduated cylinder and Eppendorf pipette, appropriate amounts of acetic acid and sulfuric acid catalyst were added to a 25 mL addition funnel (24/40 joint and stop cock for fine adjustments). The acetic acid and sulfuric acid mixture was then slowly dripped over 10 minutes (~1mL/min) into the Griffin beaker while starch was lightly agitated. The temperature was monitored during the dripping step to ensure that a stable temperature was maintained. Next, the starch and acid mixture was transferred to a 32 oz Nalgene tumbler jug with 4 to 5 marbles (to create additional mechanical/shear while rotating). The tumbler jug was placed in a PO tumbler, set at the reaction temperature, and allow to react for desired time. At the end of the reaction, the product was slowly transferred to 1000 parts of water mixing on a stir plate. An additional 800 parts of water was used to ensure full product transfer. Using a Büchner funnel and flask, the starch was de-watered. The starch cake was then washed on a filter three (3) times using 800 parts of water. The pH of the cake was tested and if not neutral (e.g., pH 5-6), then washing was continued until a neutral pH was achieved. The product cake was crumbled and allowed to dry in a hood overnight.

Example 3: Preparation of Mono- or Multi-Substituted Starch under Aqueous Conditions Anhydrous starch was slowly added to a vessel containing 170 parts water, adjusting for moisture content in the starch. The addition was performed under agitation. The pH was adjusted to 8.0-8.5 with 3% NaOH solution. Next, 3-4 drops of 30% hydrogen peroxide was added. The slurry was then pumped into a 5-neck/5L reaction flask clamped in a water bath maintained at 75-80° F. Acid anhydride reagent (which may be a single acid anhydride for a single SCFA or multiple acid anhydrides for multiple SCFAs intended to be added) was added to the slurry. For example, acetic anhydride is added if acetate is to be bound to the starch whereas acetic anhydride, propionic anhydride, and butyric anhydride are used if acetate, propionate, and butyrate are to be bound to the starch, under agitation and at a rate of 1.2 mL/min while maintaining pH 8.0-8.5 with 3% NaOH solution. After complete addition of the reagent, the reaction pH was maintained for an additional 1 hour. Then, the starch was dewatered using a Büchner funnel and flask. The cake was then re-slurried in 170 parts water and adjusted to pH 5.5 with 3N HCL solution. The material was filtered using a Buchner funnel and flask. The starch cake was washed (on a filter) with 3×100 parts water. The starch cake was crumbled and allow to dry in a hood overnight.

Example 4: Characterization of Physical Properties of the Tri-Substituted Starch Gel permeation chromatography (GPC), $^{1}$H NMR chromatography, and degree of substitution (DS) titrations were performed to characterize the structure of the tri-substituted starch, made by aqueous or anhydrous methods.

GPC was performed on an Alliance GPCV2000 instrument with a refractive index detector with the following parameters: Column set =Phenogel 10 μm, 100 Å, 103 Å, 105 Å; Injection volume=102 μL one injection, 2 replicates per sample; Mobile phase=DMSO plus 0.03 M NaNO3; Run time=50 minutes; Flow rate=1 mL/min; Column temperature=80° C.; Detector temperature=80° C.; Sample autoloader temperature=80° C.; Standards=Pullulan (180 Da to 642 kDa); Sample Concentration=20 mg in 10 mL mobile phase; Sample and Standard preparation=Samples rotated overnight (15 hours) in headspace vials with mobile phase at room temperature, heated in boiling water for 1 hour and allowed to cool to ambient temperature. Samples were then filtered with 2 μm GMF syringe filters into 4 mL LC vials.

Figure 2:
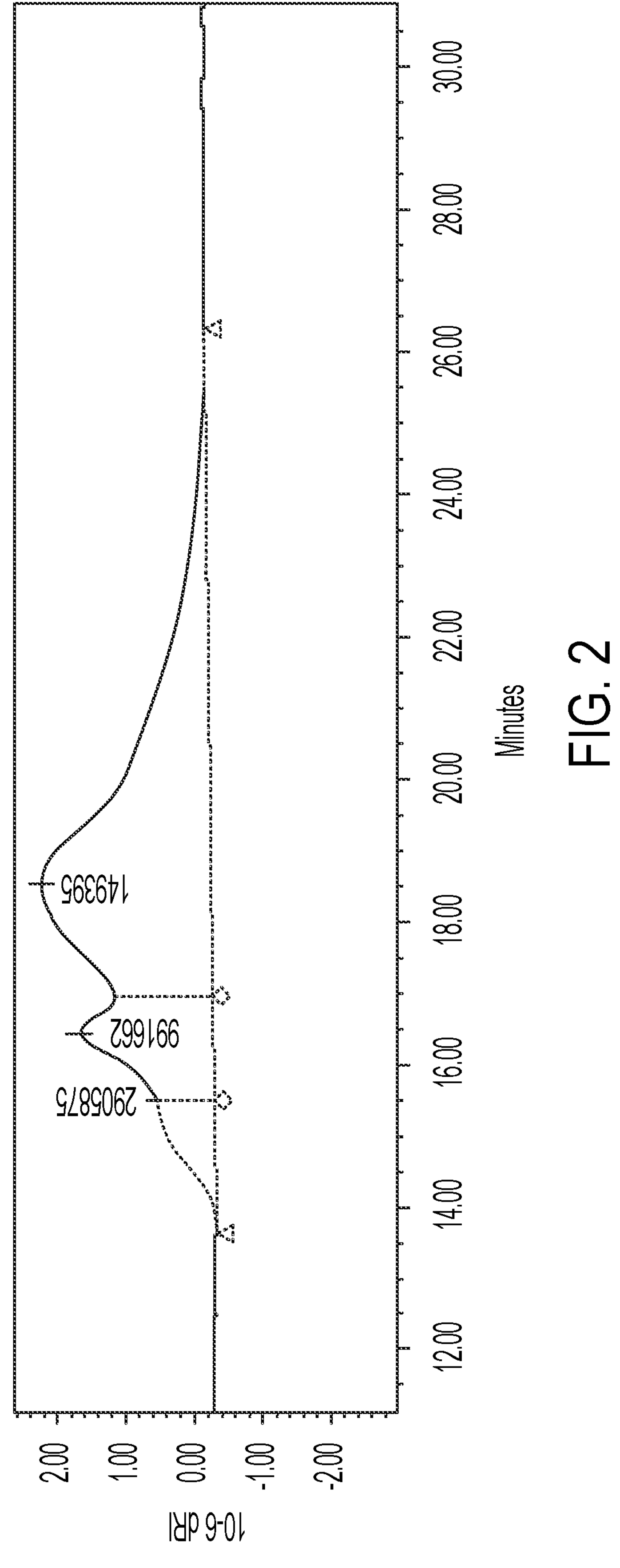
FIG. 2 shows a gel permeation chromatograph of Experimental Sample 1, a starch ester made by starch treated with acetic anhydride and having a degree of substitution of 0.2.
Figure 3:
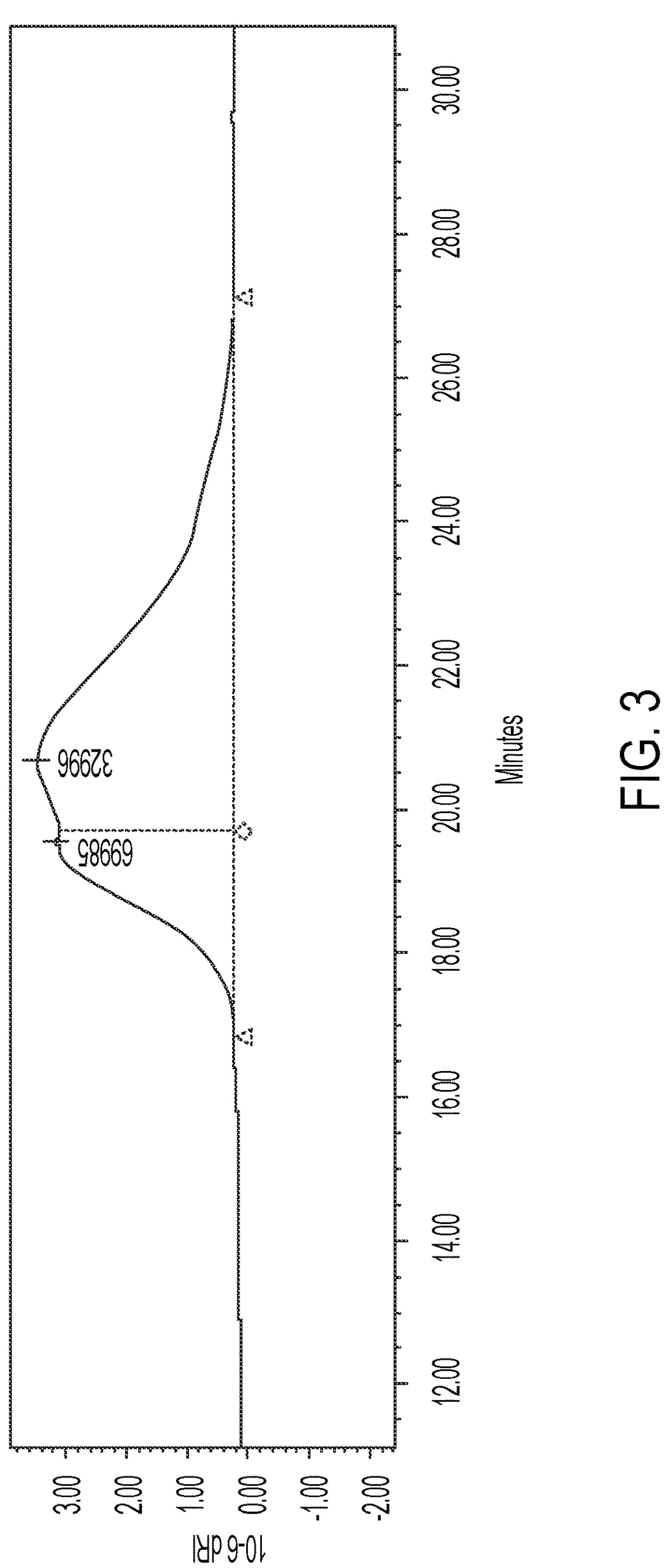
FIG. 3 shows a gel permeation chromatograph of Experimental Sample 2, a starch ester made by starch treated with acetic acid and having a degree of substitution of 0.2.
Figure 4:
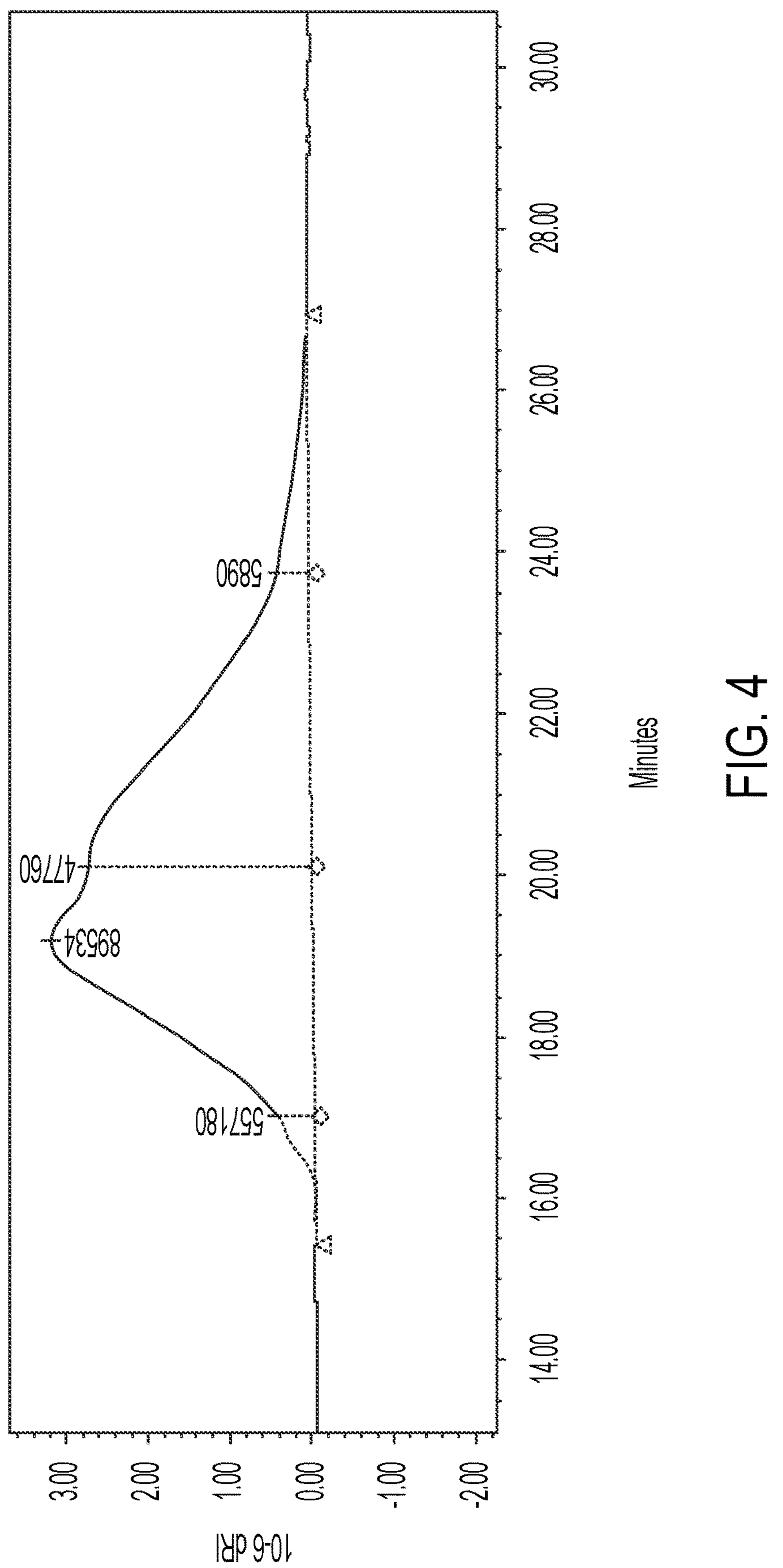
FIG. 4 shows a gel permeation chromatograph of Experimental Sample 3, a starch ester made by starch treated with acetic acid and having a degree of substitution of 0.2.

The GPC for native HYLON® VII, corn starch shows three distinct populations, with the highest molecular weight population at a retention time of 15 minutes and molecular weight of 5.6M Da (see FIG. 1). HYLON® VII starch acetate prepared by an aqueous process (Experimental Sample 1 was prepared using the protocol cited in Example 3) also exhibited three distinct populations at nominally the same retention times and molecular weight values (see FIG. 2). A difference was observed in the peak percent of the largest molecular weight population where native HYLON® VII had a larger population of higher molecular weight density than the starch acetate (14% and 6%, respectively). There were two HYLON® VII starch acetate prototypes prepared by anhydrous process with equivalent degree of substitution but differ in the amount of sulfuric acid catalyst used to prepare the sample. The sample prepared with the greater amount of catalyst (Experimental Sample 2, prepared using protocol from Example 1 with modification of using 0.5 mol % H2SO4 catalyst, 80° C., 2 hr) exhibited two distinct populations with a clear shift to lower molecular weight populations (as determined by a shift to longer retention times) (see FIG. 3). The largest recorded average molecular weight was 114,000 Da. The sample prepared with the lower amount of catalyst and longer reaction times (Experimental Sample 3, prepared using protocol from Example 1 with modification of using 0.25 mol % catalyst, 4 hr incubation at 80° C.) exhibited four distinct molecular weight populations (see FIG. 4). The retention times are slightly shifted toward longer times compared to native starch. However, compared to the sample with higher catalyst concentration, the largest recorded average molecular weight is 730,000 Da, indicating that the lesser amount of catalyst surprisingly favored esterification with minimal degradation of the molecular weight profile of the treated starch.

Figure 5A:
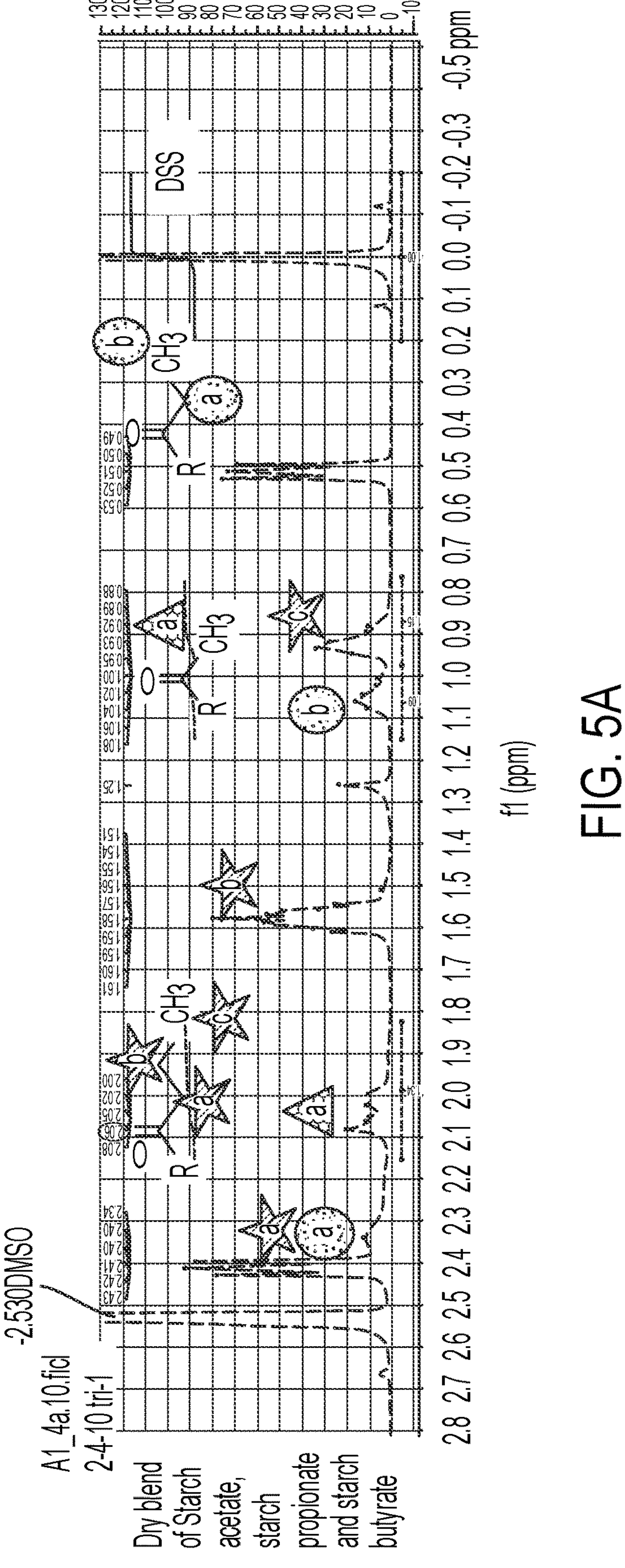
FIG. 5A shows the $^{1}$1-1 NMR analysis of a dry blend of mono-substituted starch esters: a mixture of starch acetate, starch propionate and starch butyrate, compared to FIG. 5B which shows the $^{1}$H-NMR analysis of a tri-substituted starch being substituted with acetate, propionate and butyrate.
Figure 5B:
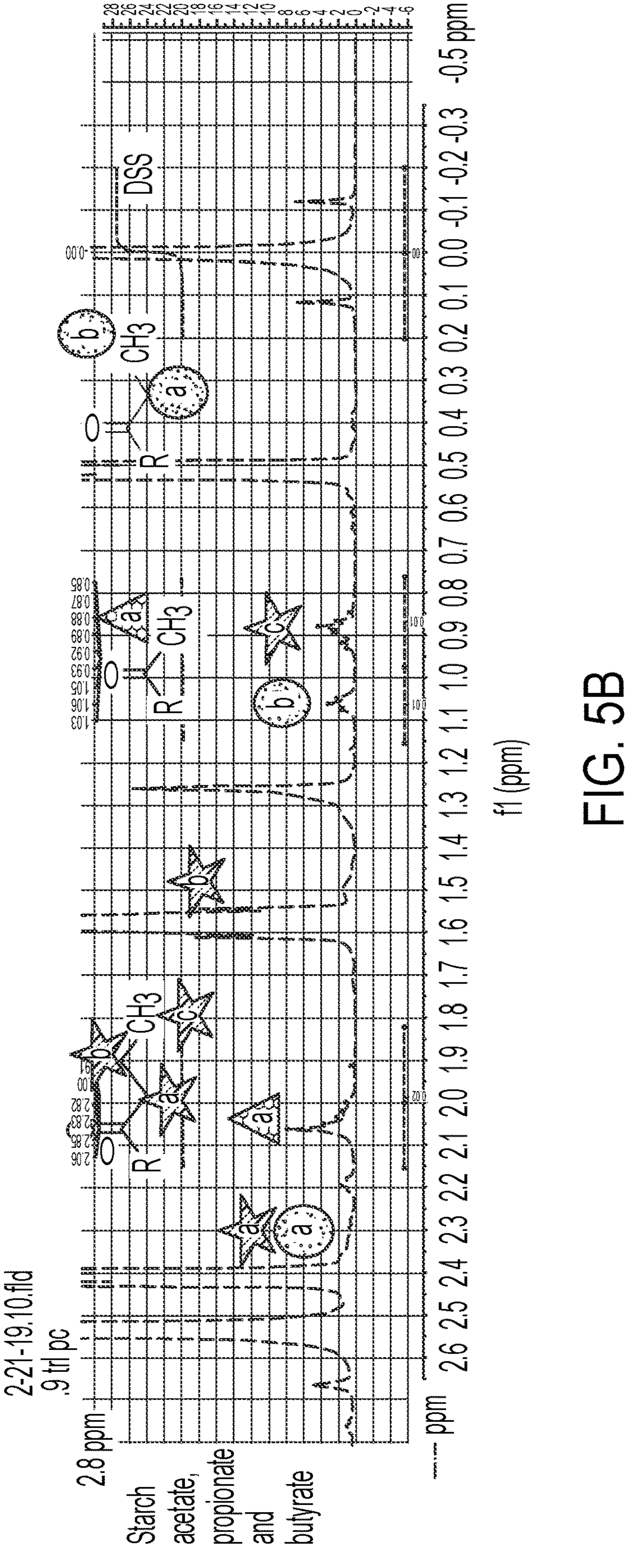

Nuclear Magnetic Resonance (NMR) spectroscopy was performed on a Bruker 500 MHz instrument. The $^{1}$H NMR spectrogram, shown in FIGS. 5A-5B, compares the results obtained from NMR treatment of a dry blend of mono-substituted starch esters (FIG. 5A, the dry blend being a mixture of HYLON® VII esterified with acetate, HYLON® VII esterified with butyrate, and HYLON® VII esterified with propionate, to provide a combination of starch acetate, starch propionate and starch butyrate mixed together) to a single tri-modified starch containing acetate, propionate and butyrate moieties (FIG. 5B).

Here, the degree of substitution was determined with a titration method. One gram of starch was transferred to a 600 mL low form beaker and 200mL of deionized water was added. The solution was cooked in a boiling water bath for 30 minutes with continuous stirring for the first 3 minutes. Next, the solution was cooled to at least 60° C. and 3-4 drops of phenolphthalein was added. The mixture was titrated with 0.1N NaOH to achieve a pink endpoint. Then, 75mL of 0.1N NaOH was added, and the solution was covered with parafilm and transferred to an incubator and allowed to incubate for 24 hr at 60° C. Next, the solution was titrated with 0.1N HCl until the endpoint was achieved; this data recorded. 1-2 mL 0.1N HCl was added in excess. The solution was covered with parafilm and placed back in the incubator at 60° C. to incubate for 1 hr. The solution was then back titrated with 0.1N NaOH to achieve a pink endpoint; this data was recorded. Calculations were made according to the following equations:

$$\% \text{ Ester (gross)} = \frac{[(\text{total mL NaOH} \times 0.1\text{N NaOH}) - (\text{total mL HCl} \times 0.1\text{N HCl})] \times (M.W. \text{ of ester})]}{(\text{anhydrous weight of starch})} \times 100$$

$$\% \text{ Ester(net)} = \text{gross ester content} - \text{blank ester content}.$$

The gross and net degrees of esterification were used to determine DS.

Example 5: Effect of DMSO on Starch Esterified with SCFA

Tri-substituted HYLON® VII, corn starch (prepared by an aqueous process) and native HYLON® VII starch (the starch base used to make the tri-substituted starch) were processed in DMSO according to the protocol described in U.S. Pat. Publ. No 2019/0167615, published Jun. 6, 2019. Micrographs of native HYLON® VII and tri-substituted HYLON® VII were taken before and after the starches were processed with DMSO. A 1% dispersion of each product was prepared in deionized water. Next, 20 μL of the dispersion was applied to a microscope slide with a micro glass cover slip. The samples were evaluated using an optical light microscope with a polarizer filter. Starch existing in a granular form is known to exhibit birefringence and a Maltese cross diffraction pattern when viewed when viewed with polarized light, as described by Thomas and Atwell, pp. 14-15 (1999). Similarly, starch in its non-granular form refers to any starch or starch derivative that has had its native granular structure disrupted or removed.

Figure 6:
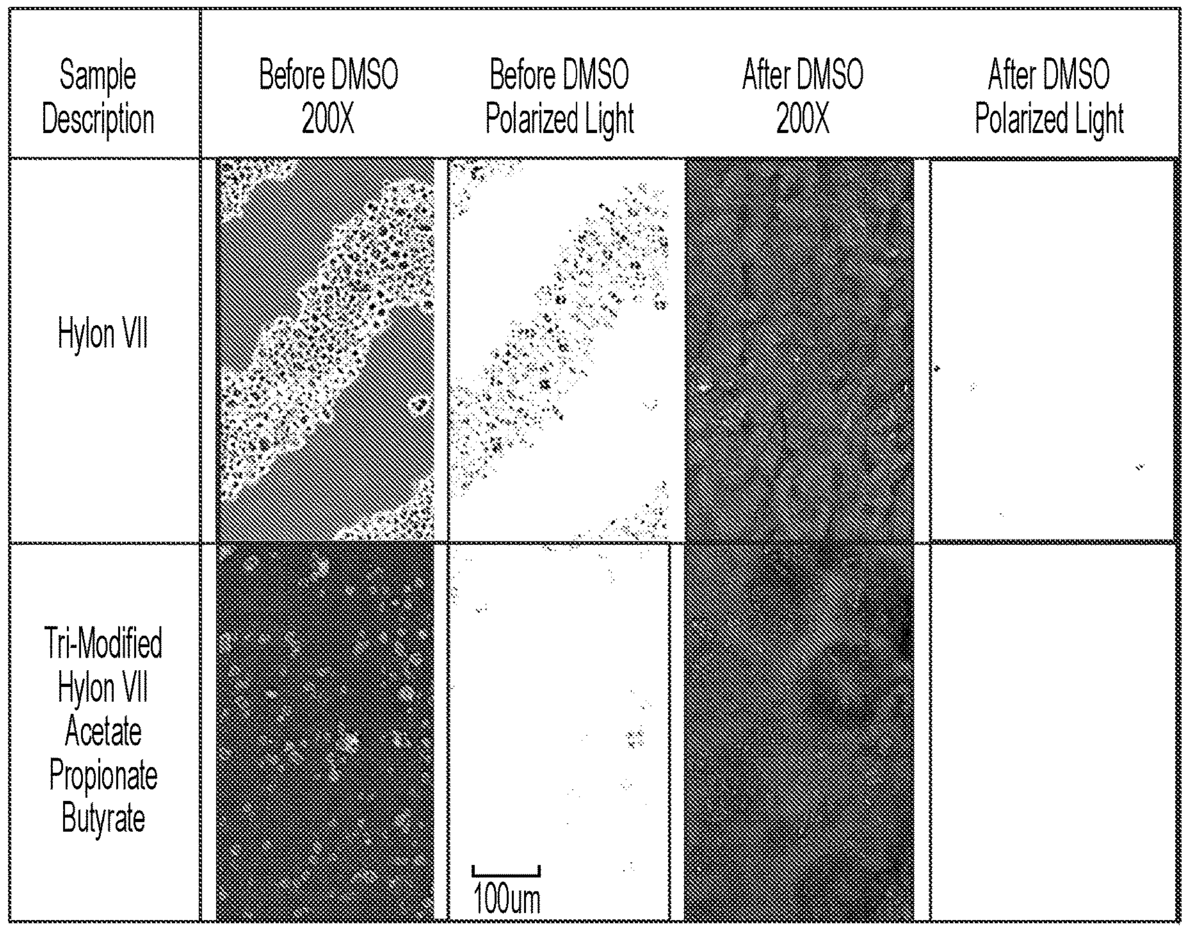
FIG. 6 shows microscopy photos of unmodified, base corn starch (HYLON® VII) and tri-substituted HYLON® VII corn starch containing acetate, propionate and butyrate. These images show the starch granules both before and after processing with DMSO.

The micrographs indicate that heating the starch in DMSO, using conditions described in U.S. Patent Publication No. 2019/0167615, resulted in the loss of birefringence and brightness (see FIG. 6). A loss of Maltese cross effect was also observed (not shown). These results indicate the loss of crystallinity and integrity in these starch granules.

The in vitro effect of DMSO treatment on the physical structure of the starch products suggests that DMSO treatment decreases or challenges the functional performance of starches. Rats fed a combination of high amylose corn starch acetylated in the presence of DMSO and unmodified corn starch (LAHAMS+MS) were compared to rats fed high amylose corn starch acetylated in the absence of DMSO and unmodified corn starch (IAHAMS+MS). The LAHAMS+MS group had both lower body weights (180 grams vs. 201 grams, respectively) and lower wet weights of caecal contents than rats fed DMSO-processed starch (IAHAMS+MS) (2.80 grams vs. 3.72 grams, respectively) (see Bird et al., *Food Hydrocolloids,* 2006, 20:1135-40). Without being bound to theory, these results may be due to the DMSO-induced loss in crystallinity from the starch products.

Example 6: Differential Scanning Calorimetry (DSC) Testing for Granular Integrity To characterize the effects of the anhydrous process on the granular integrity of the native starch base, differential scanning calorimetry was performed on native HYLON® VII, HYLON® VII acetate prepared using the aqueous process of the present invention, and HYLON® VII acetate prepared using the anhydrous process of the present invention. The results are reported in Table 1. The onset temperature is the temperature in which gelatinization begins. The enthalpy of starch gelatinization can be described as the amount of energy required to gelatinize, or cook out, one gram of starch. The maximum temperature is the highest temperature reading during the gelatinization process.

The gelatinization onset and maximum temperatures of all modified samples are lower than for native HYLON® VII. Without being bound by theory, this may occur due to weakening of hydrogen bonding caused from introduction of the short chain fatty acids, thus lowering of the gelatinization temperature. The data shows differences between the enthalpy of native HYLON® VII compared to the modified types.

TABLE 1

Starch Gelatinization determined by DSC

| Sample Name | DSC Data Starch Gelatinization | | |
|---|---|---|---|
| | Onset Temp. (° C.) | Enthalpy (J/g) | Max Temp. (° C.) |
| HYLON ® VII (FIG. 1) | 76.16 | 4.234 | 92.07 |
| Aqueous HYLON ® VII Acetate (Experimental Sample 1 (FIG. 2)) | 63.94 | 4.05 | 82.71 |
| Anhydrous HYLON ® VII Acetate (Experimental Sample 2 (FIG. 3)) | 65.56 | 1.245 | 82.44 |
| Anhydrous HYLON ® VII Acetate (Experimental Sample 4) | 64.75 | 3.215 | 85.25 |

Example 7: Characterization of Short Chain Fatty Acid Release within an In Vitro Model Colon Model An in vitro model colon study was performed to assess the beneficial effects of tri-substituted starch on the delivery of individual SCFAs to the colon, to measure the amount of individual SCFAs generated at different timepoints when colonic microbes or cells were incubated with single- or tri-substituted starch ester. The starch esters were made using the aqueous method described in Example 3.

A pool of human fecal samples (n=6) of adults aged 20-65 was used as inoculum for model colon microbe fermentations. Fecal inoculum was generated by mixing 0.1% of frozen pooled fecal material with model colon gut-like medium. The gut-like medium used for model colon fermentations was adapted from previously published colon-like medium (Macfarlane et al., *Microbial Ecology,* 1998, 35:180-187) and included in distilled water: experimental starch, mucin (porcine gastric type III) at 4.0 g/L, casein at 3.0 g/L, peptone water at 5.0 g/L, tryptone at 5.0 g/L, bile salts No. 3 at 0.4 g/L, yeast extract at 4.5 g/L, $FeSO_4 \cdot 7H_2O$ 0.005 g/L, NaCl at 4.5 g/L, KCl at 4.5 g/L, $KH_2PO_4$ at 0.5 g/L, $MgSO_4 \cdot 7H_2O$ at 1.25 g/L, $CaCl_2 \cdot 6H_2O$ at 0.15 g/L, $NaHCO_3$ at 1.5 g/L, cysteine at 0.8 g/L, hemin at 0.05 g/L, Tween 80 at 1.0 g/L.

Starch products, such as tri-substituted starch, were applied from stock concentrations of 10 mM (low), 20 mM (medium), or 40 mM (high); 100 μl of starch solution was added to 900 $_1$1.1 of gut medium containing fecal samples. The assays were performed in duplicate. Incubations were performed for 20 hours, with the starch fibers resuspended after 6h of fermentation. Samples were taken at 6 hr and 20 hr and placed in solution organic acid concentrations for using high-performance liquid chromatography (HPLC) analysis, to measure the levels or amounts of different SCFA present in the assays. A 6 hr timepoint is representative of a short transit time within the digestive system (e.g. as with for a patient suffering from diarrhea). A 20 hr time is representative of longer transit time within the digestive system. The results are shown in FIGS. 7 through 10.

In FIGS. 7-10, each column indicates the average or mean levels of individual SCFAs generated in under various experimental conditions. In FIGS. 7-9, each column is accompanied by a black bar that indicates the amount of SCFA produced an experimental sample, adjusted for starch content. FIGS. 7-9 compare the effects of a mono-substituted starch ester, tri-substituted starch ester, and a mixture of acetylated starch, butyrated starch, and priopionated starch on the model colon assays, various starch esters listed in Table 2. HAMSA is a high amylose corn starch which is acetylated. HAMSB is a high amylose corn starch which is butylated. HAMSP is high amylose corn starch which is propionated. HAMSABP is a high amylose corn starch which is acetylated, butylated and propionated.

TABLE 2

Compositions for starch esters

| Starch ester | Starch and esterified SCFA |
|---|---|
| HAMSA | HYLON ® VII esterified with acetate |
| HAMSB | HYLON ® VII esterified with butyrate |
| HAMSP | HYLON ® VII esterified with propionate |
| HAMSABP | HYLON ® VII esterified with acetate, butyrate, and propionate |
| Dry blend | Mixture of HYLON ® VII esterified with acetate, HYLON ® VII esterified with butyrate, and HYLON ® VII esterified with propionate |

Figure 7A:
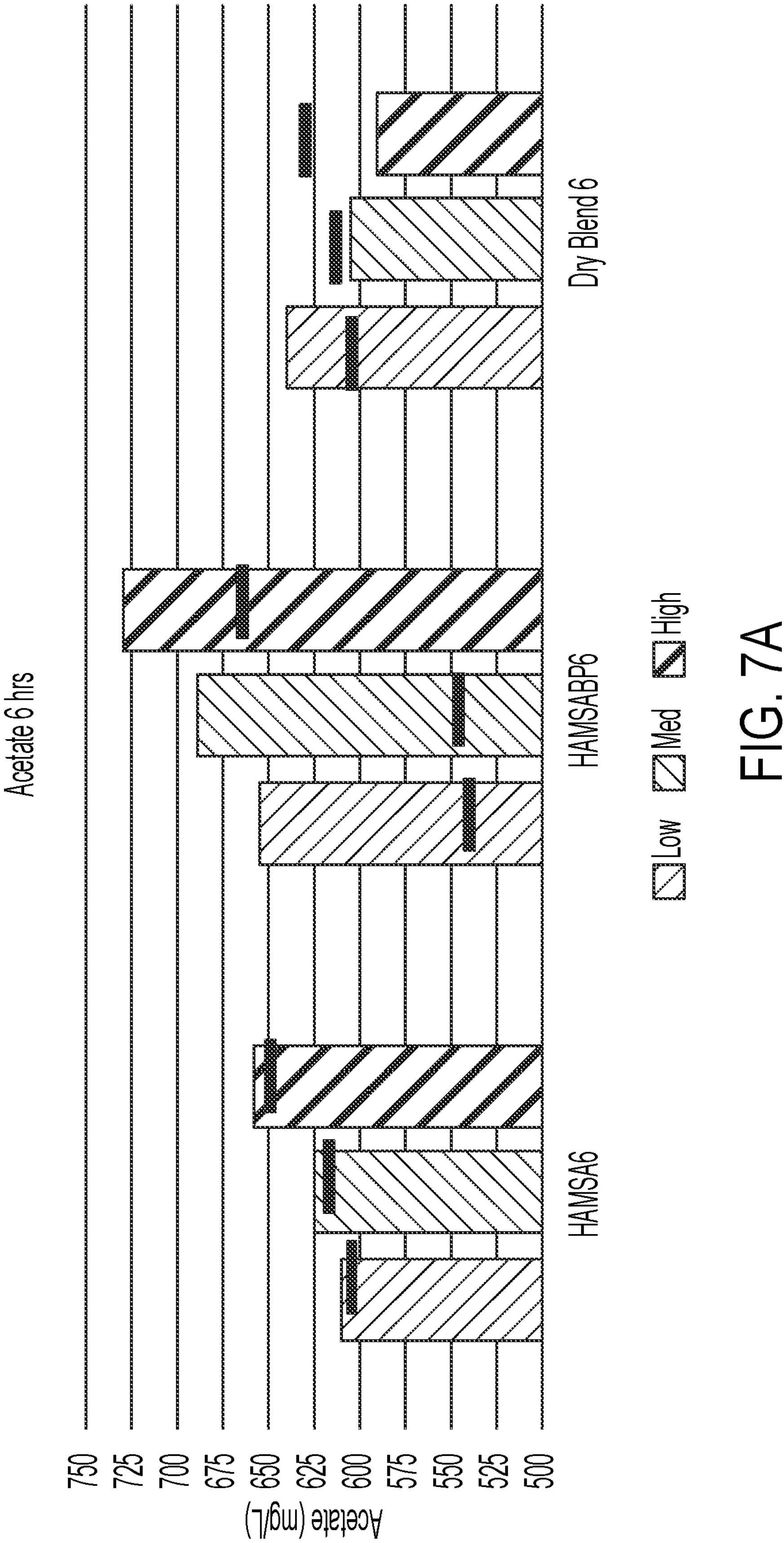
FIG. 7A shows measurements of acetate levels at 6 hours after incubation of starch esters in an in vitro model colon study. The effect of starch acetate (HAMSA6, HYLON® VII esterified with acetate) is compared to the effects of both tri-substituted starch (HAMSABP6, HYLON® VII esterified with acetate, propionate and butyrate) and a dry blend of mono-substituted starch esters: starch acetate, starch propionate and starch butyrate (Dry Blend, a mixture of HYLON® VII esterified with acetate, HYLON® VII esterified with butyrate, and HYLON® VII esterified with propionate). Samples were made using stock concentrations of 10 mM (low), 20 mM (medium), or 40 mM (high).

FIG. 7 shows the effect of various treatments on the amount of acetate produced by model colon microbes when the microbes were incubated in the presence of low, medium, and high concentrations of acetylated starch, tri-substituted starch, or a mixture of mono-substituted starch esters. As shown in FIG. 7A, after 6 hours of incubation, colonic microbes incubated in the presence of acetylated starch (HAMSA6, which was made from HYLON® VII esterified with acetate) generated acetate levels (see columns) slightly greater than the amount of acetate bound to the starch ester (see accompanying bars). In comparison, the presence of tri-substituted starch (HAMSABP6, which was made from HYLON® VII esterified with acetate, propionate and butyrate) induced acetate levels (columns) that were greater than the amount of acetate bound to the tri-substituted starch ester (accompanying bars). The dry blend of mono-substituted starch esters (Dry Blend 6) yielded levels of acetate that were similar to or less than those present in acetylated starch (HAMSA6).

Figure 7B:
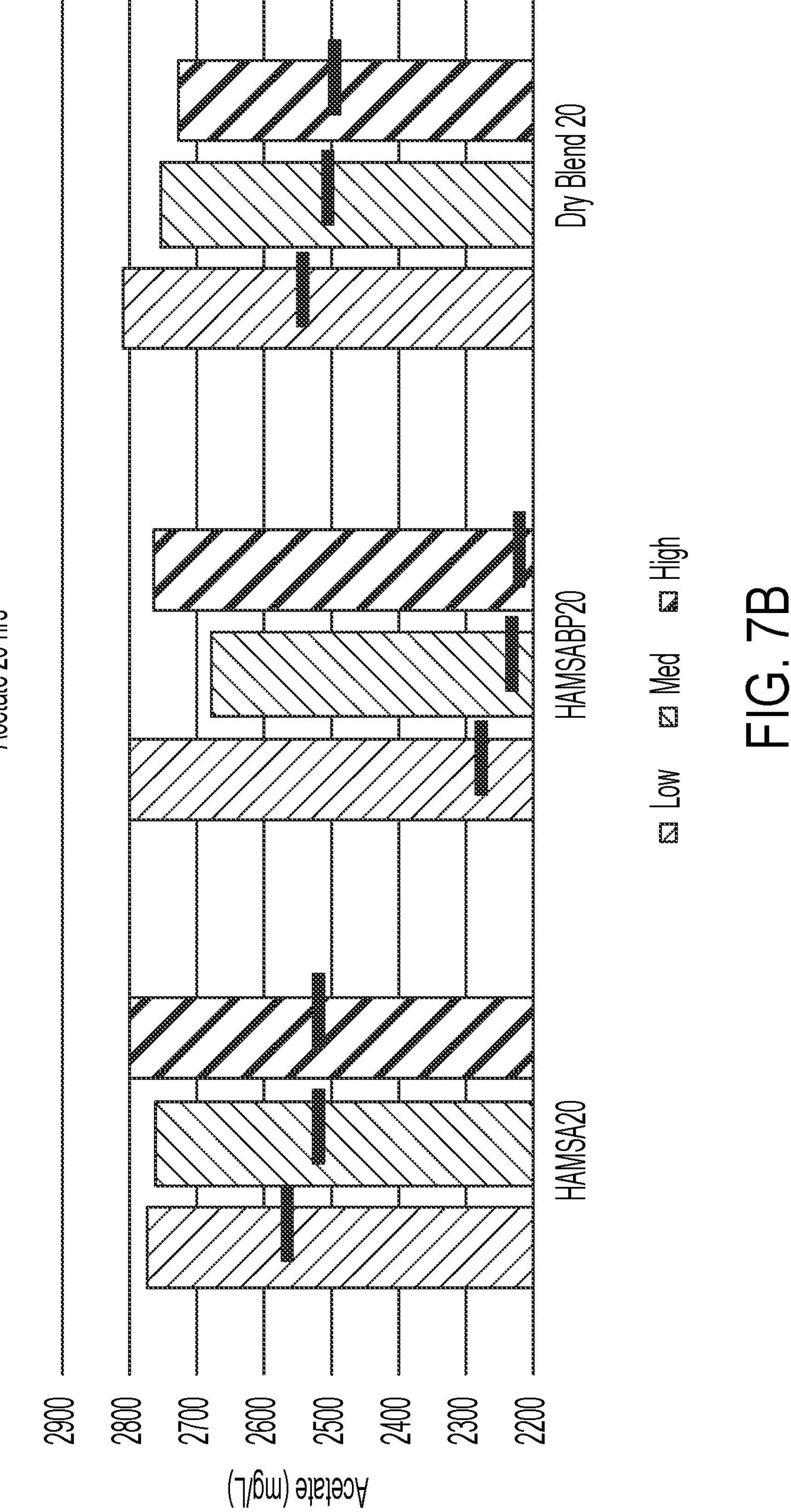
FIG. 7B shows acetate levels measured at 20 hours of incubation with the in vitro model colon study.

As shown in FIG. 7B, after 20 hours of incubation, all three compounds elicited amounts of acetate that exceeded the amount of acetate present in the treatment compounds. However, the tri-substituted starch ester (HAMSABP20) elicited greater amounts of acetate than the other compounds (HAMSA20 and Dry Blend 20). Taken together, FIGS. 7A-7B show that treatment with the tri-substituted starch ester induced levels of acetate greater than the amount of acetate provided by the tri-substituted starch ester itself. While some of the acetate measured could have been generated as a breakdown product of the starch ester added to the model colon assay, these results suggest that at least a portion of the acetate levels were the result of acetate produced by the microbes in the assay. Without being bound to theory, the increased amount of acetate may be due to the tri-substituted starch ester inducing acetate production in the model colon microbes.

Table 3 shows the distribution of acetate in the model colon assay at various timepoints, where acetate can remain bound to a starch ester or can be released from the starch ester into the gut-like medium, after the fecal inoculum was exposed to starch modified only with acetate, tri-substituted starch, or a blend of mono-substituted starch esters; starch acetate, starch propionate and starch butyrate. To calculate bound acetate, $^{1}$H NMR analysis was first used to determine the individual mass % of starch base and acetate. Next, GC-FIID was used to quantify released acetic acid. The difference was calculated by subtracting the bound amount from the released amount.

TABLE 3

Calculated free vs. bound acetate in mg/L at the high concentration tested.

| | Bound | Released |
|---|---|---|
| Acetate 6 hr | | |
| HAMSA | 48.495 | 14.785 |
| HAMSABP | 41.38 | 162.69 |
| Dry blend | 15.124 | 4.61 |
| Acetate 20 hr | | |
| HAMSA | 48.495 | 295.49 |
| HAMSABP | 41.38 | 561.43 |
| Dry blend | 15.124 | 248.20 |

Figure 8A:
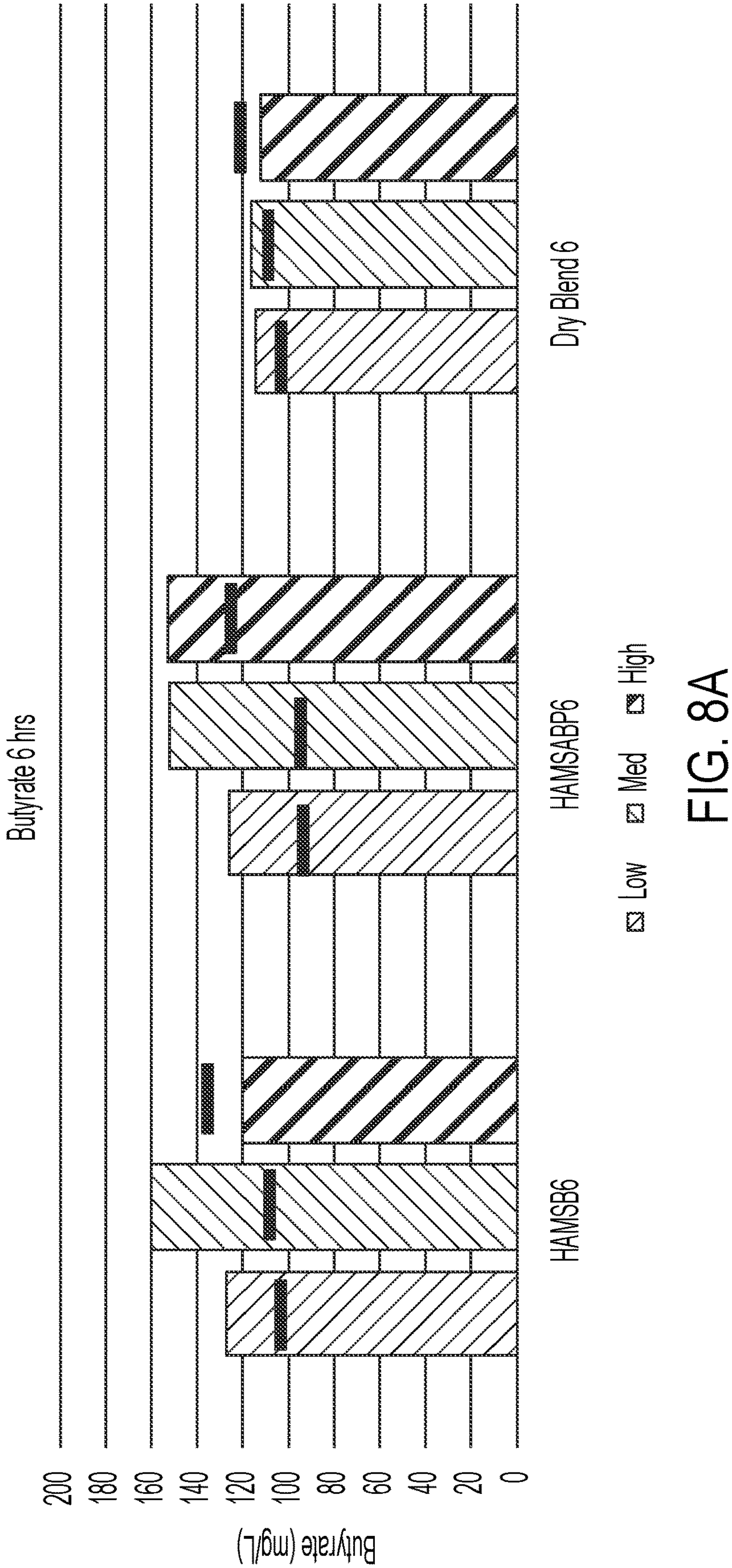
FIG. 8A shows measurements of butyrate levels at 6 hours after incubation of starch esters with an in vitro model colon study. The effect of starch butyrate (HAMSB6, HYLON® VII esterified with butyrate) is compared to the effects of both tri-substituted starch (HAMSABP6, HYLON® VII esterified with acetate, propionate and butyrate) and a dry blend of mono-substituted starch esters: starch acetate, starch propionate and starch butyrate (Dry Blend, the Dry Blend being a mixture of HYLON® VII esterified with acetate, HYLON® VII esterified with butyrate, and HYLON® VII esterified with propionate). Samples were made using stock concentrations of 10 mM (low), 20 mM (medium), or 40 mM (high).
Figure 8B:
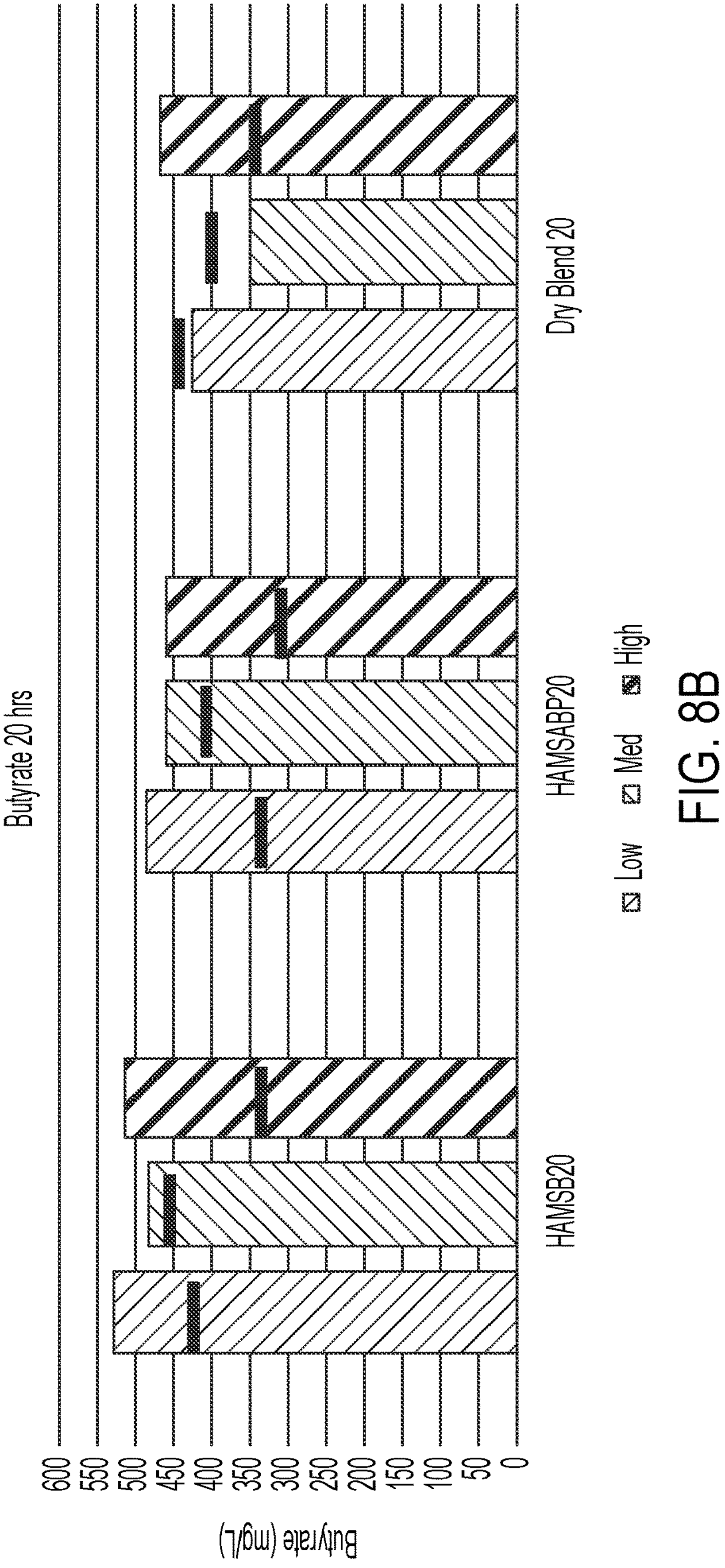
FIG. 8B shows butyrate levels measured at 20 hours of incubation with an in vitro model colon study.

FIG. 8A-8B shows the effect of various treatments on the amount of butyrate produced by colonic microbes when the microbes are incubated in the presence of low, medium, and high concentrations of butyrated starch, tri-substituted starch, or a mixture of mono-substituted starch esters. As shown in FIG. 8A, after 6 hours of incubation, colonic microbes incubated in the presence of butyrated starch (HAMBA6, which was made from HYLON® VII esterified with butyrate) or the mixture of mono-substituted starch esters (Dry Blend 6) generated moderate amounts of butyrate above the levels of butyrate bound to the starch esters (see accompanying bars); at the highest concentrations of added starch ester, the model colon microbes showed a net loss of butyrate. In comparison, the presence of low, medium, and high levels of tri-substituted starch (HAMSABP6, which was made from HYLON® VII esterified with acetate, propionate and butyrate) induced butyrate levels (columns) that were much greater than the levels of butyrate bound to the tri-substituted starch ester (accompanying bars). As shown in FIG. 8, after 20 hours of incubation, Table 4 shows the distribution of butyrate in the model colon assay at various timepoints, where butyrate can remain bound to a starch ester or can be released from the starch ester into the gut-like medium, after the fecal inoculum was exposed to starch modified only with butyrate, tri-substituted starch, or a blend of mono-substituted starch esters; starch acetate, starch propionate and starch butyrate. To calculate bound butyrate, $^{1}$H NMR analysis was first used to determine the individual mass % of starch base and butyrate. Next, GC-FIID was used to quantify released butyric acid. The difference was calculated by subtracting the bound amount from the released amount.

TABLE 4

| Calculated free vs. bound butyrate in mg/L at the high concentration tested. | | |
|---|---|---|
| | Bound | Released |
| Butyrate 6 hr | | |
| HAMSB | 63.441 | −19.95* |
| HAMSABP | 64.859 | 28.27 |
| Dry blend | 23.084 | −27.51* |
| Butyrate 20 hr | | |
| HAMSB | 63.441 | 166.39 |
| HAMSABP | 64.859 | 173.66 |
| Dry blend | 23.084 | 122.03 |

*Released values are calculated based on difference between butyrate generated by control (unmodified Hylon VII) and experimental modified samples (mono- and tri-substituted Hylon VII). A negative value indicates that the control sample produced more butyrate.

Figure 9A:
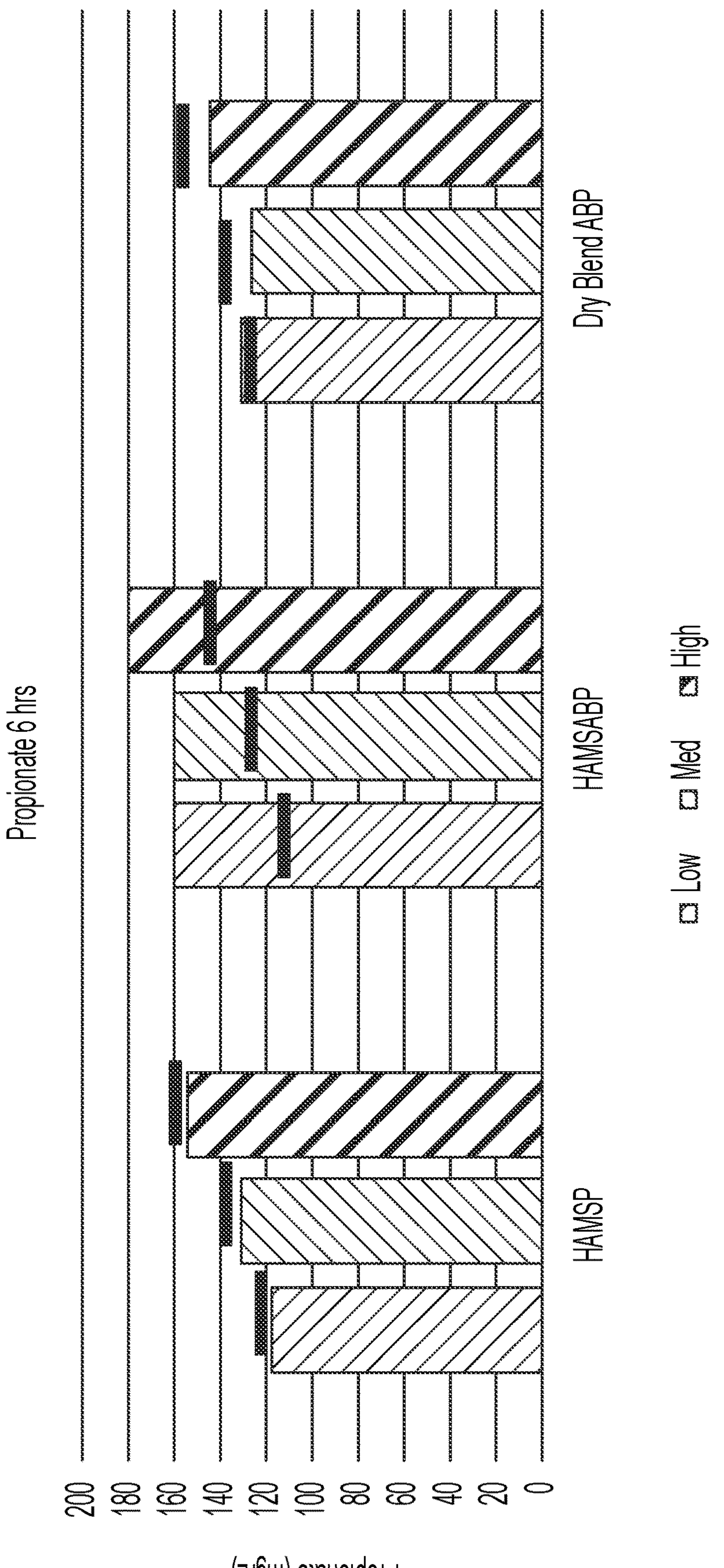
FIG. 9A shows measurements of propionate levels at 6 hours after incubation of starch esters with an in vitro model colon study. The effect of starch propionate (HAMSP6, HYLON® VII esterified with propionate) is compared to the effects of both tri-substituted starch (HAMSABP6, HYLON® VII esterified with acetate, propionate and butyrate) and a dry blend of mono-substituted starch esters: starch acetate, starch propionate and starch butyrate (Dry Blend ABP, the Dry Blend being a mixture of HYLON® VII esterified with acetate, HYLON® VII esterified with butyrate, and HYLON® VII esterified with propionate). Samples were used from stock concentrations of 10 mM (low), 20 mM (medium), or 40 mM (high).
Figure 9B:
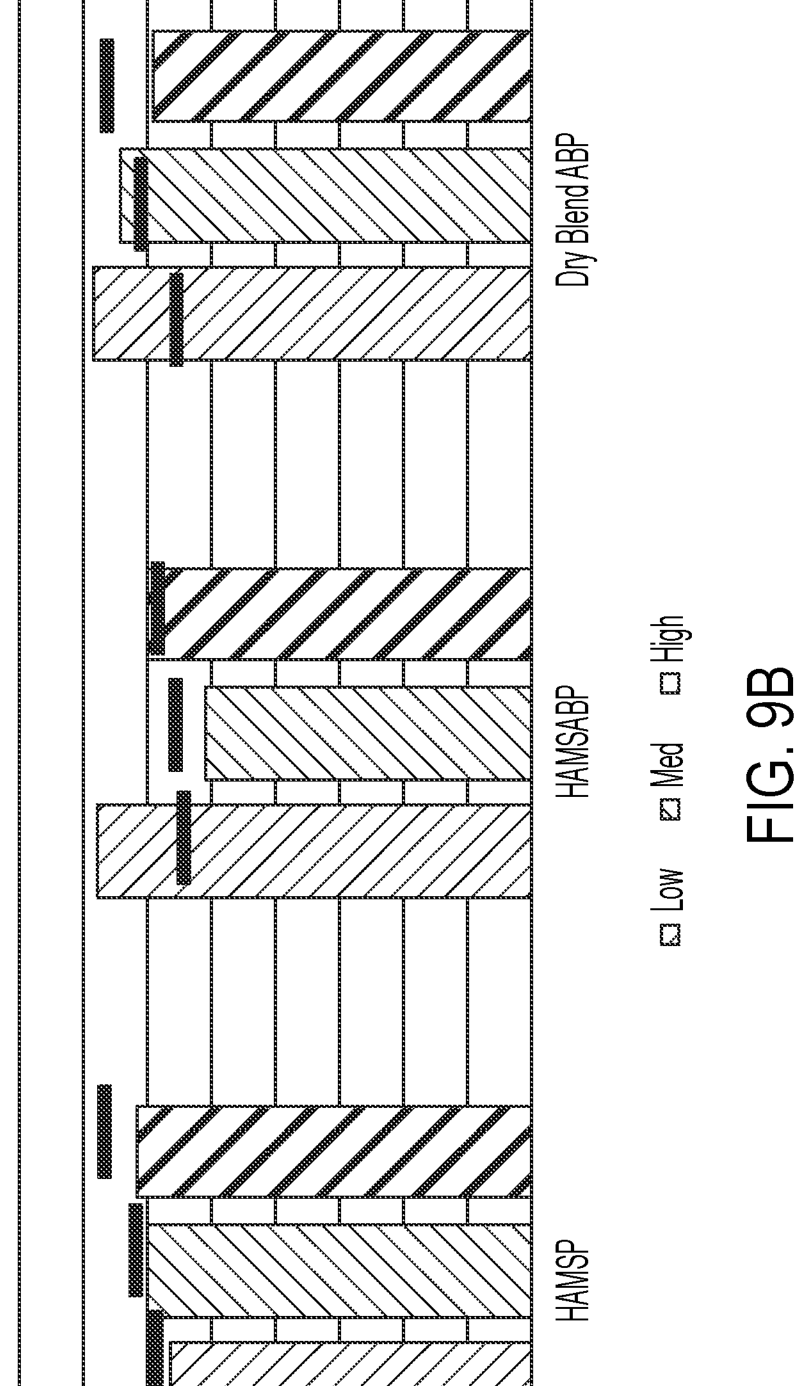
FIG. 9B shows propionate levels measured at 20 hours of incubation with an in vitro model colon study.

FIGS. 9A-9B shows the effect of various treatments on the amount of propionate produced by model colon microbes when the microbes are incubated in the presence of low, medium, and high concentrations of propionated starch, tri-substituted starch, or a mixture of mono-substituted starch esters. As shown in FIG. 9A, after 6 hours of incubation, colonic microbes incubated in the presence of propionated starch (HAMBP6, which was made from HYLON® VII esterified with propionate) or the mixture of mono-substituted starch esters (Dry Blend 6) showed a net decrease in the amounts of propionate above the levels of propionate bound to the starch esters (see accompanying bars), except for the lowest level of Dry Blend which displayed a marginal increase in propionate levels. In comparison, the presence of low, medium, and high levels of tri-substituted starch (HAMSABP6, which was made from HYLON® VII esterified with acetate, propionate and butyrate) induced propionate levels (columns) that were much greater than the levels of propionate bound to the tri-substituted starch ester (accompanying bars). As shown in FIG. 9B, the effect of the tri-substituted starch was less pronounced compared to the effect of the other comparators after 20 hours of incubation.

While some of the propionate measured could have been generated as a breakdown product of the starch ester added to the model colon assay, these results suggest that at least a portion of the propionate levels were the result of propionate production by the microbes in the assay. Without being bound to theory, these results may be due to the tri-substituted starch ester inducing propionate production in the model colon microbes.

Figure 10A:
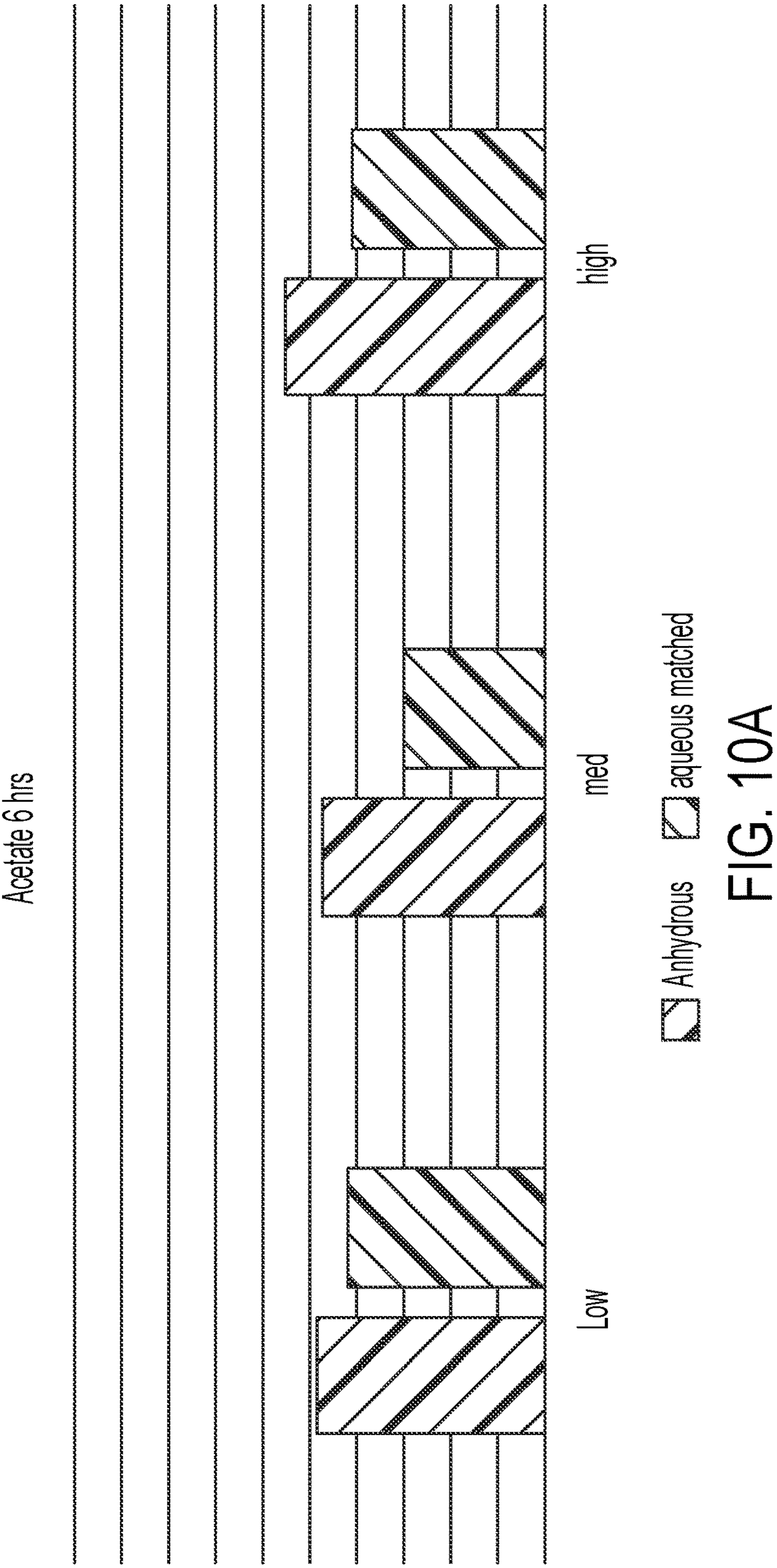
FIG. 10A shows measurements of acetate levels in an in vitro model colon study after incubation with starch acetate compositions prepared by different processes, measured at 6 hours of incubation. The effect of starch acetate prepared using an anhydrous method is compared to the effect of starch acetate prepared using an aqueous method. Samples were used from stock concentrations of 10 mM (low), 20 mM (med), or 40 mM (high).
Figure 10B:
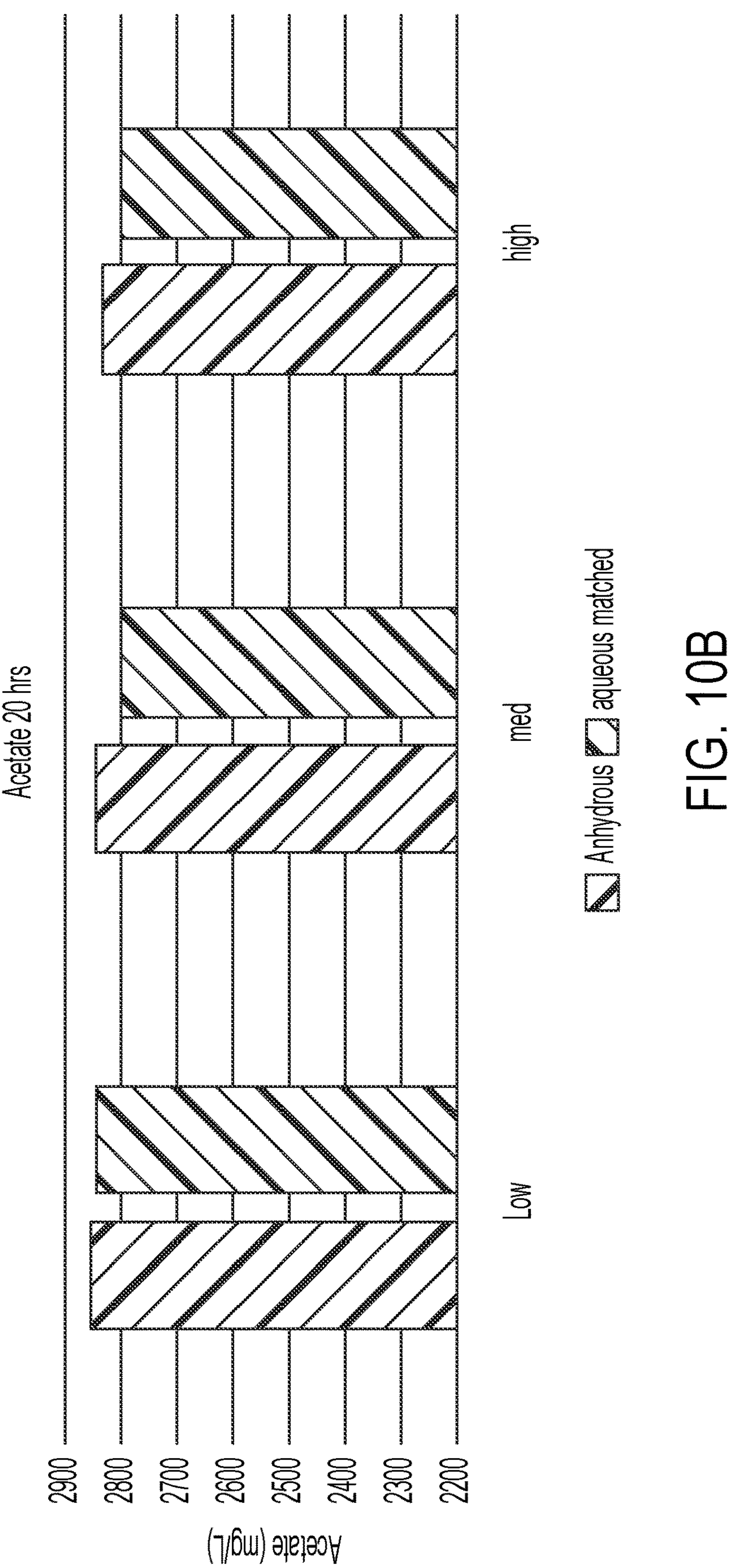
FIG. 10B shows acetate levels measured at 20 hours of incubation with anhydrous prepared or aqueous prepared starch acetate within in the in vitro model colon study.

To examine the effect of starch esterification procedures on SCFA release in in vitro model colon assay, acetate-substituted starch molecules prepared by either the aqueous method or the anhydrous process were applied to the in vitro model colon assay. The results are shown in FIG. 10. At 6 hours, starch acetates produced from the anhydrous process yielded acetate in higher amount than starch acetates produced from the aqueous process.

What is claimed is:

1. A starch ester comprising a starch esterified with at least three short chain fatty acids selected from the group consisting of formate, acetate, propionate, butyrate, isobutyrate, valerate, and isovalerate, wherein the starch ester has a degree of substitution of about 0.01 to about 0.6; and wherein the starch ester is in an effective amount to induce a first amount of a short chain fatty acid in an in vitro model colon assay greater than a second amount of the short chain fatty acid provided by a control composition, the control composition comprising a monosubstituted or di-substituted starch ester.

2. The starch ester of claim 1, wherein the starch ester contains less than 1% dimethyl sulfoxide.

3. The starch ester of claim 1, wherein the starch ester contains less than 0.1% dimethyl sulfoxide.

4. The starch ester of claim 1, wherein the starch ester has a crystalline granular structure.

5. The starch ester of claim 1, wherein the starch ester is incubated in the in vitro model colon assay for about 0.5 hour.

6. The starch ester of claim 1, wherein the starch ester requires between about 0.1 to about 10.0 J/g 5 to gelatinize one gram of the starch ester, compared to a control starch molecule that is not esterified.

7. A method for producing a starch ester of claim 1, the method comprising;

a) mixing a starch with at least three short chain fatty acids;

b) adding an esterification catalyst, to provide a mixture;

c) mixing the mixture; and d) optionally, heating the mixture;

wherein the method is performed in the absence of DMSO.

8. The method of claim 7, wherein the at least three short chain fatty acids are acetate, propionate, and butyrate.

9. The method of claim 7, wherein the method is performed under anhydrous conditions.

10. The method of claim 7, wherein the starch ester has a degree of substitution of about 0.05 to about 0.5, about 0.1 to about 0.4, about 0.1 to about 0.3, or about 0.2 to about 0.3; and wherein the starch ester is in a crystalline granular structure.

11. The method of claim 7, wherein the esterification catalyst is selected from the group consisting of sulfuric acid, perchloric acid, hydrochloric acid, methane sulfonic acid, dodecyl benzene sulfonic acid, benzene sulfonic acid, toluene sulfonic acid, strong-acid ion exchange resin, phosphoric acid, and mixtures thereof; and wherein the esterification catalyst is used at between about 0.1 and about 1.0 mol %, between about 0.1 and about 0.8 mol %, between about 0.1 and about 0.6 mol %, between about 0.1 and about 0.5 mol %, between about 0.2 and 1. about 0 mol %, between about 0.2 and about 0.8 mol %, or between about 0.25 and about 0.5 mol %.

12. The method of claim 7, wherein the starch ester comprises at least three short chain fatty acids selected from the group consisting of from formate, acetate, propionate, butyrate, isobutyrate, valerate, and isovalerate.

13. The starch ester of claim 1, obtainable by the method of claim 7.

14. A composition comprising the starch ester of claim 1.

15. A method for providing a nutritional supplement in support of gut health in a subject, the method comprising administering to the subject an effective amount of the starch ester as described in claim 1.

16. A method for inhibiting an autoimmune or metabolic disorder in a subject in need thereof, the method comprising administering to the subject an effective amount of the starch ester as described in claim 1, wherein the disorder is selected from the group consisting of obesity, diabetes, inflammation, inflammatory bowel disease, irritable bowel syndrome, diarrhea, atherosclerosis, Crohn's disease and ulcerative colitis.

17. The starch ester of claim 1, wherein the at least three short chain fatty acids are acetate, propionate, and butyrate.

* * * * *